United States Patent
Ring et al.

(10) Patent No.: US 12,195,532 B2
(45) Date of Patent: **\*Jan. 14, 2025**

(54) HIGH AFFINITY SIRP-ALPHA REAGENTS AND METHODS OF USING

(71) Applicant: The Board of Trustees of the Leland Stanford Junior University, Stanford, CA (US)

(72) Inventors: Aaron Michael Ring, New Haven, CT (US); Kenan Christopher Garcia, Menlo Park, CA (US); Kipp Andrew Weiskopf, Brookline, MA (US); Aron M. Levin, Cambridge, MA (US); Irving L Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 223 days.

This patent is subject to a terminal disclaimer.

(21) Appl. No.: 17/530,287

(22) Filed: Nov. 18, 2021

(65) Prior Publication Data
US 2022/0064293 A1    Mar. 3, 2022

Related U.S. Application Data

(63) Continuation of application No. 15/912,471, filed on Mar. 5, 2018, now Pat. No. 11,208,481, which is a (Continued)

(51) Int. Cl.
*A61K 38/16* (2006.01)
*C07K 14/47* (2006.01)
(Continued)

(52) U.S. Cl.
CPC ...... *C07K 16/2803* (2013.01); *C07K 14/4703* (2013.01); *A61K 38/16* (2013.01);
(Continued)

(58) Field of Classification Search
None
See application file for complete search history.

(56) References Cited

U.S. PATENT DOCUMENTS

| 6,541,615 B1 | 4/2003 | Ullrich et al. |
| 7,691,970 B2 | 4/2010 | Skerra et al. |
| | (Continued) | |

FOREIGN PATENT DOCUMENTS

| CN | 102257001 A | 11/2011 |
| JP | 2011/500005 | 1/2011 |
| | (Continued) | |

OTHER PUBLICATIONS

Zhang et al., SIRP/CD47 Signaling in Neurological Disorders, Brain Res. 14; 1623: 74-80, Oct. 2015.*
(Continued)

*Primary Examiner* — Claire Kaufman
(74) *Attorney, Agent, or Firm* — Pamela J. Sherwood; Bozicevic, Field & Francis LLP

(57) ABSTRACT

High affinity SIRP-α reagent are provided, which (i) comprise at least one amino acid change relative to the wild-type protein; and (ii) have an increased affinity for CD47 relative to the wild-type protein. Compositions and methods are provided for modulating phagocytosis in a mammal by administering a therapeutic dose of a pharmaceutical composition comprising a high affinity SIRPα reagent, which blocks the physiological binding interaction between SIRPα and its ligand CD47.

10 Claims, 17 Drawing Sheets
Specification includes a Sequence Listing.

Related U.S. Application Data continuation of application No. 14/371,370, filed as application No. PCT/US2013/021937 on Jan. 17, 2013, now Pat. No. 9,944,911.

(60) Provisional application No. 61/587,247, filed on Jan. 17, 2012.

(51) Int. Cl.
    *C07K 16/28* (2006.01)
    *C07K 16/46* (2006.01)
    *A61K 38/17* (2006.01)
    *G01N 33/50* (2006.01)

(52) U.S. Cl.
    CPC ...... *A61K 38/1774* (2013.01); *C07K 2317/52* (2013.01); *C07K 2319/30* (2013.01); *C12Y 301/03048* (2013.01); *G01N 33/5005* (2013.01)

(56) References Cited

U.S. PATENT DOCUMENTS

| | | | |
|---|---|---|---|
| 10,406,179 B2* | 9/2019 | Shizuru | C07K 16/2803 |
| 10,894,831 B2* | 1/2021 | Schnorr | C07K 16/2896 |
| 11,419,189 B2* | 8/2022 | Kim | H05B 6/062 |
| 11,608,377 B2* | 3/2023 | Schnorr | C07K 14/525 |
| 2007/0148201 A1 | 6/2007 | Skerra et al. | |
| 2010/0239579 A1 | 9/2010 | Smith et al. | |
| 2011/0237498 A1 | 9/2011 | Raymond et al. | |

FOREIGN PATENT DOCUMENTS

| | | | | |
|---|---|---|---|---|
| WO | WO2000/077026 | 12/2000 | | |
| WO | WO2009/046541 | 4/2009 | | |
| WO | WO2010070047 | 6/2010 | | |
| WO | WO2010/130053 | 11/2010 | | |
| WO | WO-2013109752 A1 * | 7/2013 | ............. | A61P 35/00 |

OTHER PUBLICATIONS

Xie et al., An agonistic anti-signal regulatory protein alpha antibody for chronic inflammatory diseases, Cell Reports Med. 4:101130, Aug. 15, 2023.*

GenBank Database, Accession No. NP_037148, Tyrosine-protein phosphatase non-erceptor type substrate 1 precurson, [Rattus norvegicu], accessed on Mar. 14, 2017, verson NP_037148.2, Sep. 1, 2016.

Hatherly et al., "Structure of signal-regulatory protein alpha: a link to antigen receptor evolution", J Bioi Chem, Sep. 25, 2009, pp. 26613-26619, 284(39), American Society for Biochemistry and Molecular Biology, Rockville, MD.

Hatherly et al., "The structure of the macrophage signal regulatory protein alpha (SIRPalpha) inhibitory receptor reveals a binding face reminiscent of that used by T cell receptors.", J. Bioi Chem, May 11, 2007, pp. 14567-14575, 282(19), American Society for Biochemistry and Molecular Biology, Rockville, MD.

Hatherly et al. (2008) Paired receptor specificity explained by structures of signal regulatory proteins alone and complexed with CD47, Mol. Cell, 31, 266-277.

Lee et al., "Novel structural determinants on SIRP alpha that mediate binding to CD47", J Immunol. Dec. 1, 2007, pp. 7741-7750, vol. 179, Issue 11, The American Association of Immunologists, Inc., Rockville, MD.

Lee et al., "The role of cis dimerization of signal regulatory protein alpha (SIRPalpha) in binding to CD47", J. Bioi Chem., Dec. 3, 2010, pp. 37953-37963, 285(49) American Society for Biochemistry and Molecular Biology, Rockville, MD.

Liu et al, "Functional Elements of SIRPa lgV Domain Mediate Cell Surface Binding to CD47", Journal of Molecular Biology, Jan. 19, 2007, pp. 680-693, vol. 365, Issue 3, Elsevier, Amsterdam, Netherlands.

Liu et al., "Peptide-mediated inhibition of neutrophil transmigration by blocking CD47 interactions with signal regulatory protein alpha", J Immunol., Feb. 15, 2004, pp. 2578-2585, vol. 172, Issue 4, The American Association of Immunologists, Inc., Rockville, MD.

Nakaishi et al., "Structural insight into the specific interaction between murine SHPS-1/SIRP alpha and its ligand CD47.", J Mol Bioi., Jan. 18, 2008, pp. 650-660, vol. 375, Issue 3, Elsevier, Amsterdam, Netherlands.

Takenaka et al., "Polymorphism in SIRPa modulates engraftment of human hematopoietic stem cells", Nat. Immunol., Nov. 4, 2007, pp. 1313-1323 , 8(12), Macmillan Publishers Limited, Basingstoke, United Kingdom.

Tsai et al., "Self inhibition of phagocytosis: the dictates potency of inhibition but only at low expression levels", Blood Cells Mol Dis., Jun. 15, 2010, pp. 67-74, vol. 45, Issue 1, Elsevier, Amsterdam, Netherlands.

Weiskopf, et al.: "Engineered SIRP[alpha] variants as Immunotherapeutic Adjuvants to Anticancer Antibodies", Science, Jul. 5, 2013, pp. 88-91, vol. 341, Issue 6141, American Association for the Advancement of Science, Washington, D.C.

Yamao et al., "Mouse and human SHPS-1: molecular cloning of cDNAs and chromosomal localization of genes", Biochem. Biophys. Res. Commun., Feb. 3, 1997, pp. 61-67, vol. 231, Issue 1, Elsevier, Amsterdam, Netherlands.

Zhao et al., "CD47-signal regulatory protein-a (SIRPa) interactions form a barrier for antibody-mediated tumor cell destruction.", Proc Natl Acad Sci USA, Nov. 2011, pp. 18342-18347, 108(45), National Academy of Sciences, Washington, D.C.

* cited by examiner

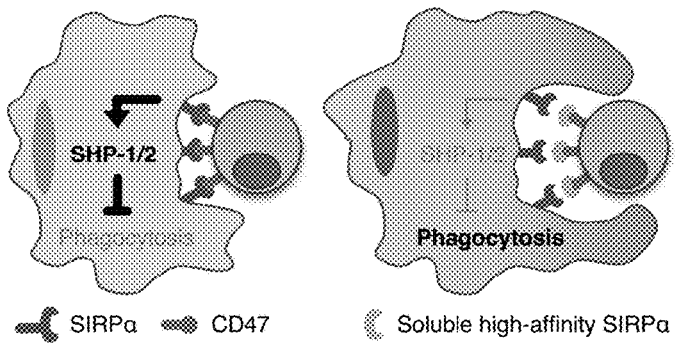
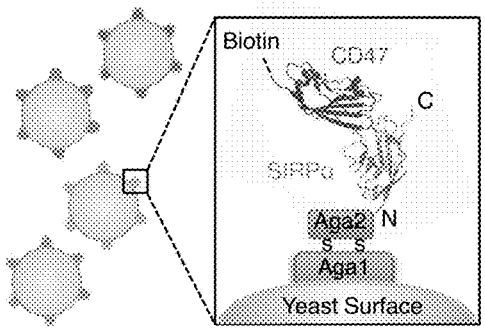
FIG. 1A  FIG. 1B
FIG. 1C
| | 4 | 6 | 21 | 27 | 31 | 47 | 53 | 54 | 56 | 63 | 66 | 68 | 92 | 94 | 103 | $K_D$ |
|---|---|---|---|---|---|---|---|---|---|---|---|---|---|---|---|---|
| WT allele 1 | L | V | A | V | I | E | K | E | H | V | S | K | V | F | F | 279 nM |
| WT allele 2 | | | A | | | | | | | | L | | | | | 452 nM |
| 1D4 | | | | | | | | | | | | R | | | V | 11.6 nM |
| 1A5 | V | | L | | | V | | | | | | R | | | | 3.6 nM |
| 2D3 | V | | V | | T | L | | | | | | R | | L | | 847 pM |
| 2A10 | | | | | S | V | | | | | | | | L | | 500 pM |
| 2B5 | I | | V | | | V | | | R | | | | V | | V | 423 pM |
| 2A2 | V | | | | | V | | | R | | | R | | L | | 402 pM |
| 2F5 | V | L | | | | V | | | | | | | | | V | 276 pM |
| FB3 | | | | | | L | | | | | | | | | | 69.9 pM |
| FD6 | V | | | | | V | | | | | | R | | | | 41.3 pM |
| FA4 | | | | | T | V | | | | | | R | | | V | 34.0 pM |
| Consensus (CV1) | | | | | | V | | | | | | | | | | 11.1 pM |
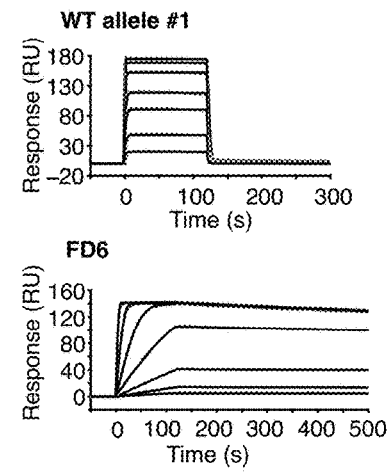
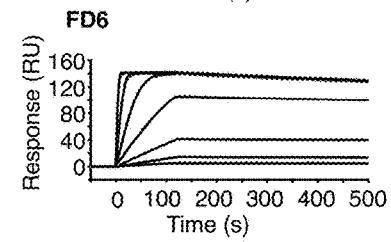
FIG. 1D  FIG. 1E
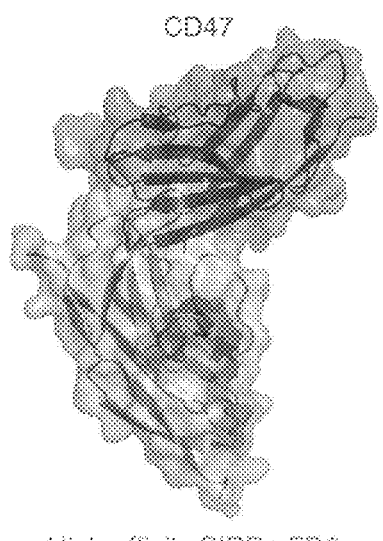
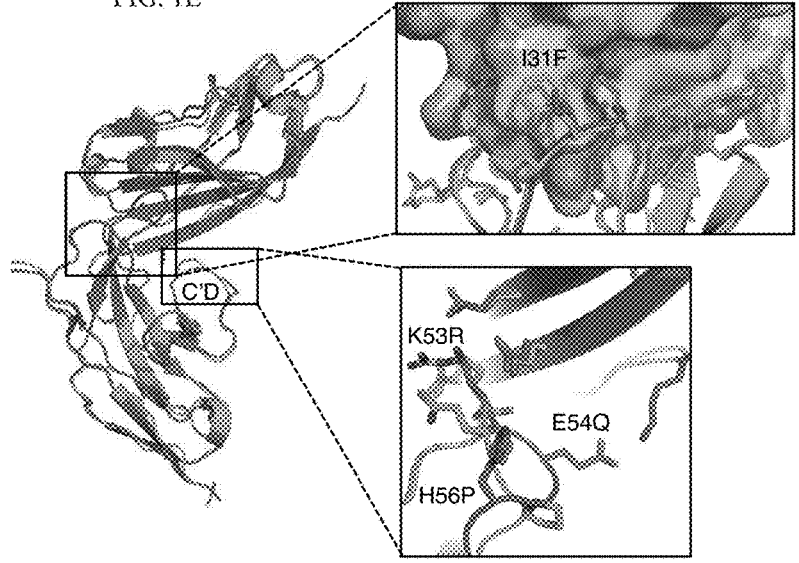

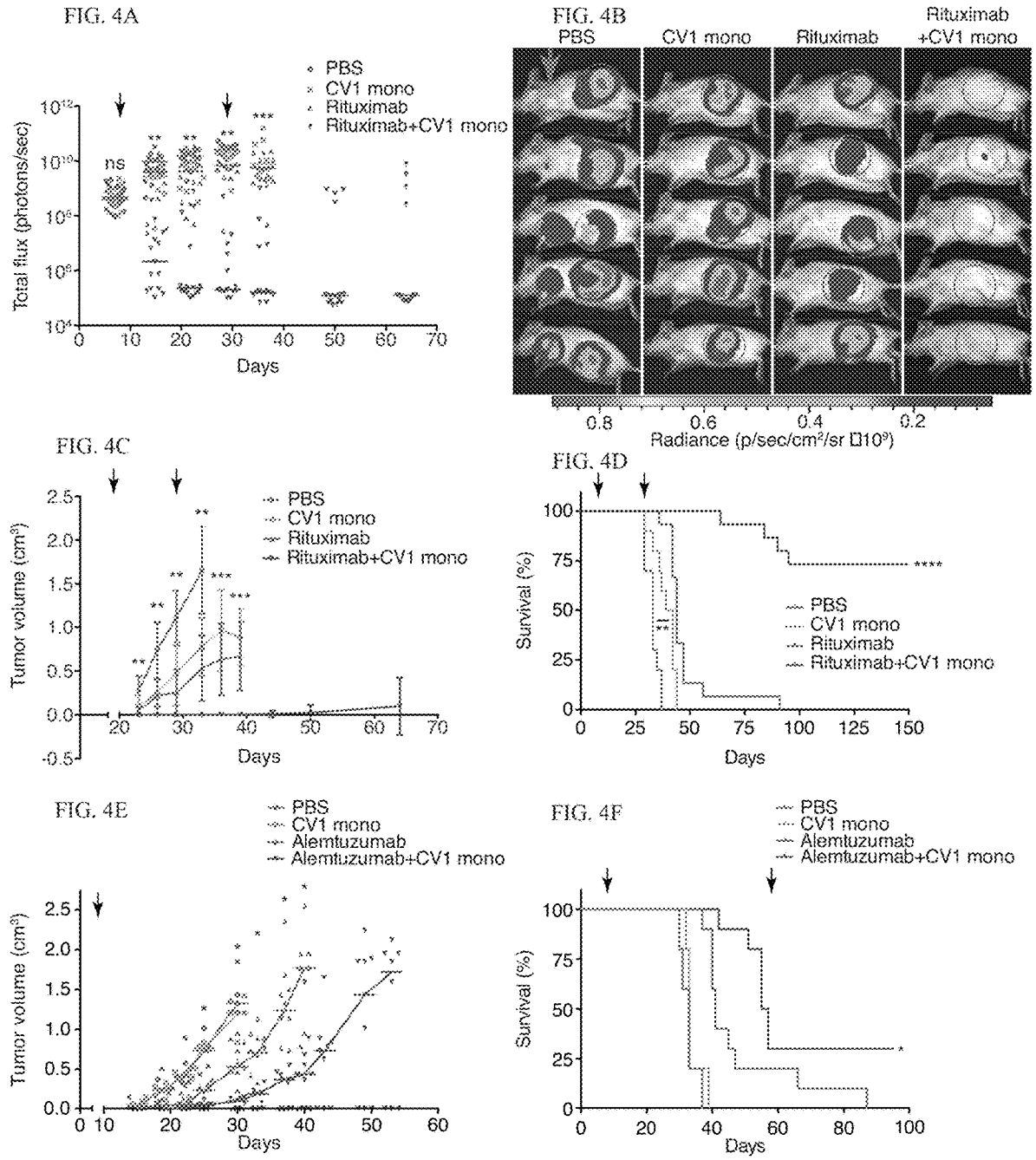

FIG. 10A

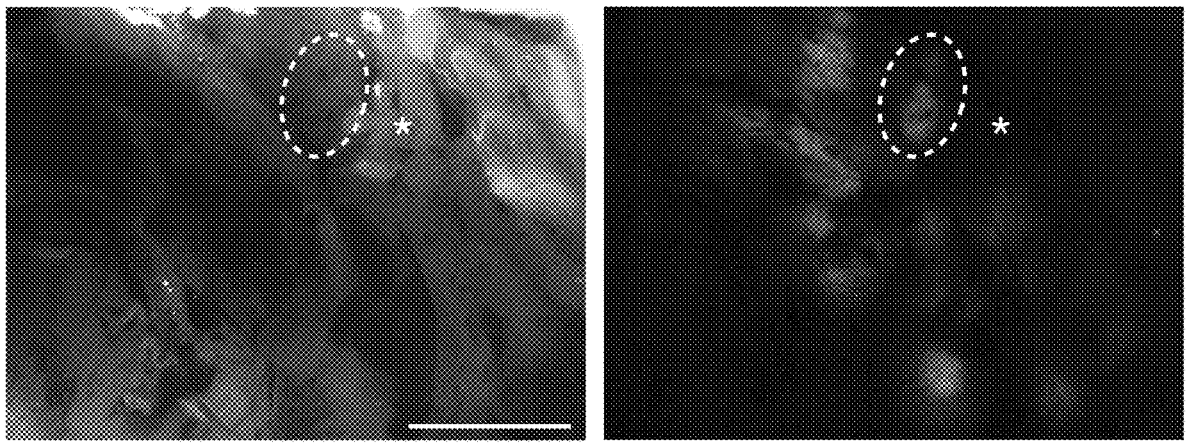

FIG. 10B

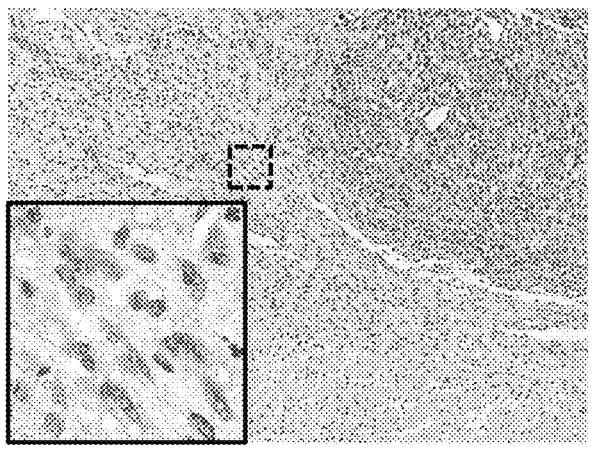

FIG. 10C

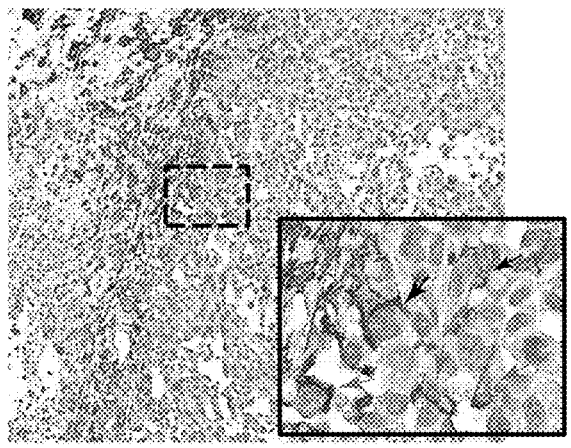

FIG. 10D

| | Unit | Normal range | | PBS | | CV1-hIgG4 | | p value |
|---|---|---|---|---|---|---|---|---|
| | | Low | High | Average | Std Dev | Average | Std Dev | |
| Total White Blood Cells | 10³/μL | 2.60 | 10.10 | 6.94 | 4.84 | 5.64 | 2.17 | 0.599 |
| Lymphocytes | 10³/μL | 1.30 | 8.40 | 2.44 | 1.43 | 1.14 | 0.66 | 0.102 |
| Monocytes | 10³/μL | 1.10 | 0.30 | 0.72 | 0.48 | 0.54 | 0.11 | 0.440 |
| Granulocytes | 10³/μL | 0.40 | 2.00 | 3.78 | 3.20 | 3.96 | 1.86 | 0.916 |
| Hematocrit | % | 32.80 | 48.00 | 37.60 | 3.80 | 30.42 | 2.72 | 0.009 |
| Mean Corpuscular Volume | fL | 42.30 | 55.90 | 44.42 | 0.68 | 45.62 | 2.39 | 0.311 |
| Red Cell Distribution Width | % | 0.00 | 99.90 | 29.40 | 0.73 | 32.78 | 5.11 | 0.181 |
| Hemoglobin | g/dL | 10.00 | 16.10 | 13.50 | 1.47 | 11.04 | 1.04 | 0.016 |
| Mean Corpuscular Hemoglobin Conc. | g/dL | 29.50 | 35.10 | 35.96 | 1.15 | 36.38 | 0.97 | 0.551 |
| Total Red Blood Cells | 10⁶/μL | 6.50 | 10.10 | 8.46 | 0.87 | 6.69 | 0.79 | 0.010 |
| Mean Corpuscular Hemoglobin | pg | 13.70 | 18.10 | 15.96 | 0.43 | 16.56 | 0.66 | 0.126 |
| Platelets | 10³/μL | 250.00 | 1540.00 | 466.80 | 102.59 | 389.80 | 108.09 | 0.281 |
| Mean Platelet Volume | fL | 0.00 | 99.90 | 5.78 | 0.49 | 5.84 | 0.35 | 0.829 |

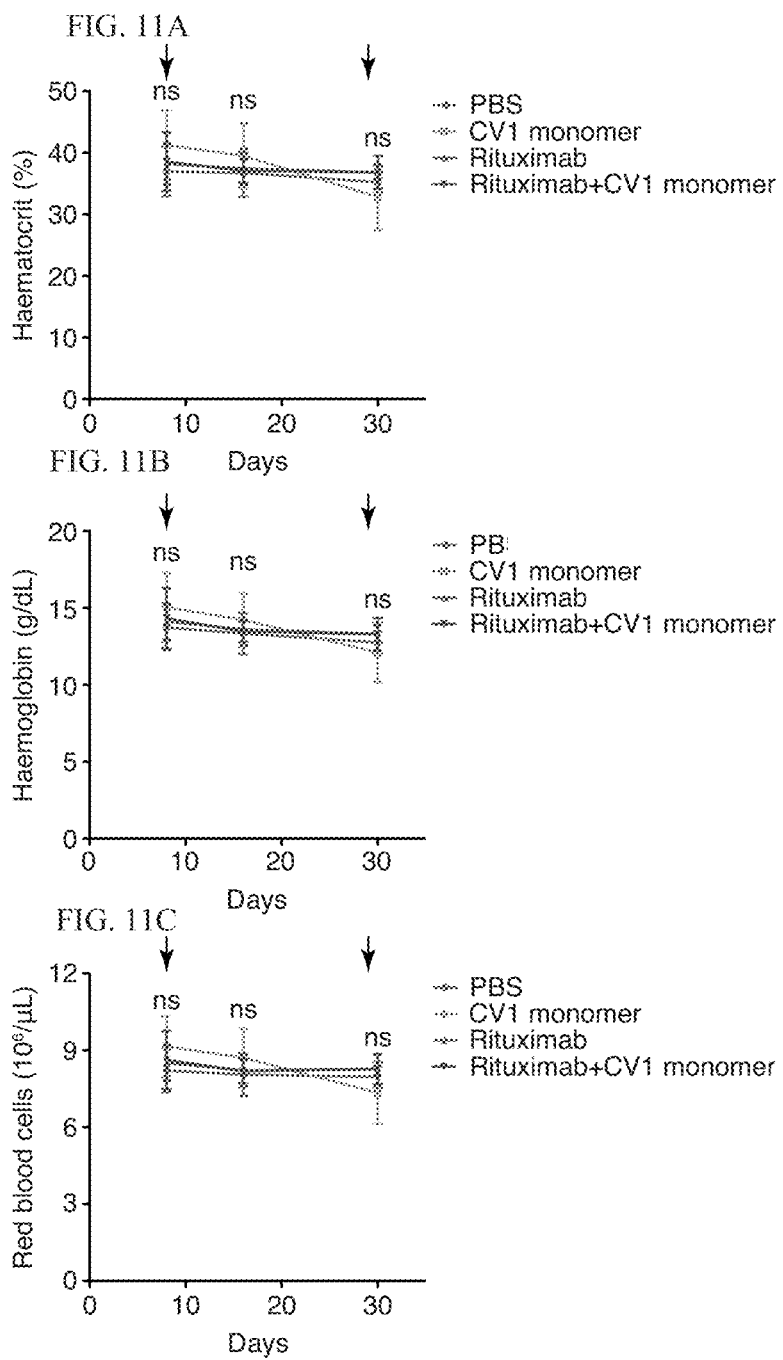

FIG. 13A
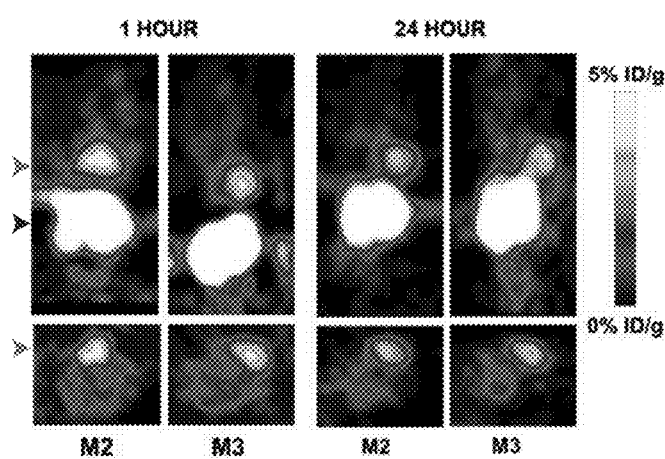
FIG. 13B
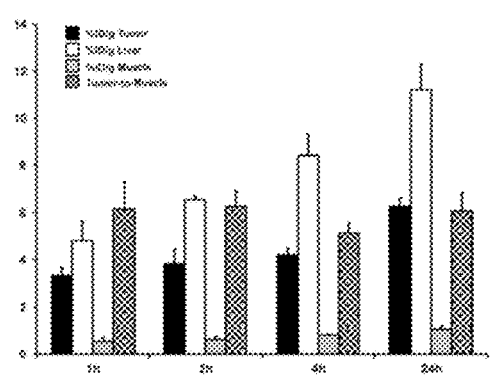
FIG. 13C

FIG. 14A
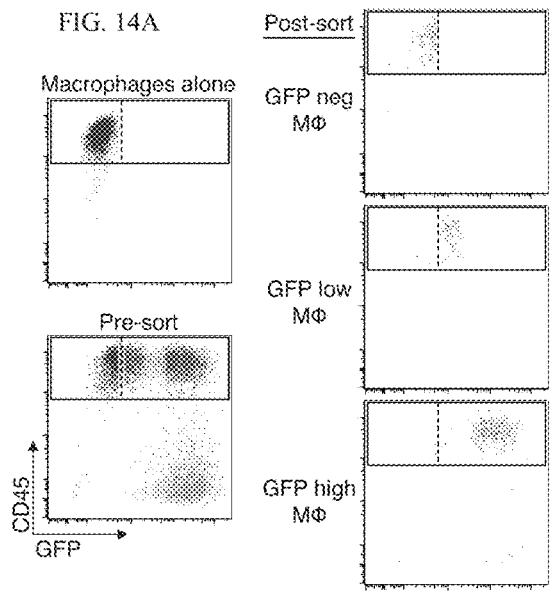
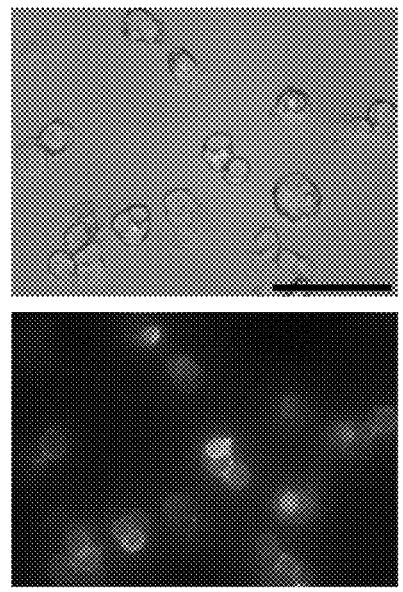
FIG. 14C
FIG. 14D
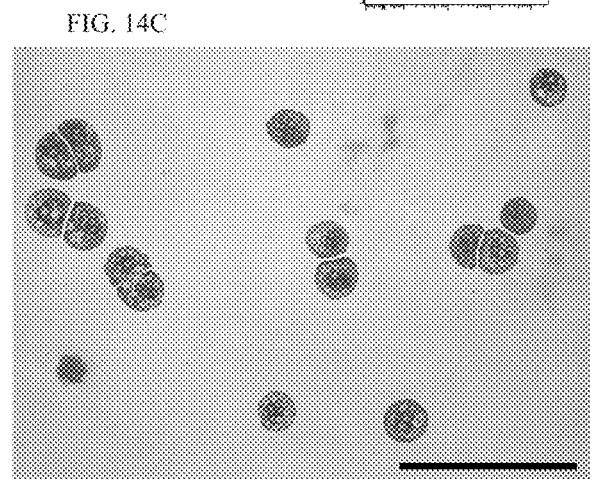
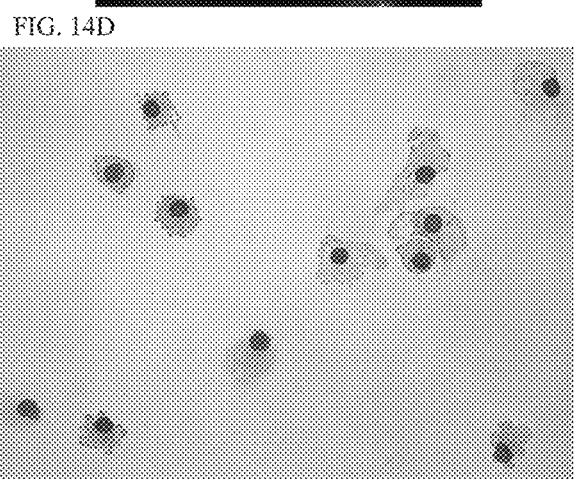
FIG. 14E
FIG. 14F
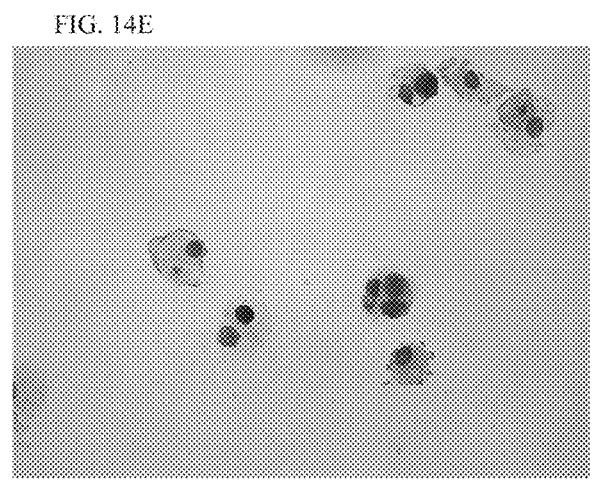
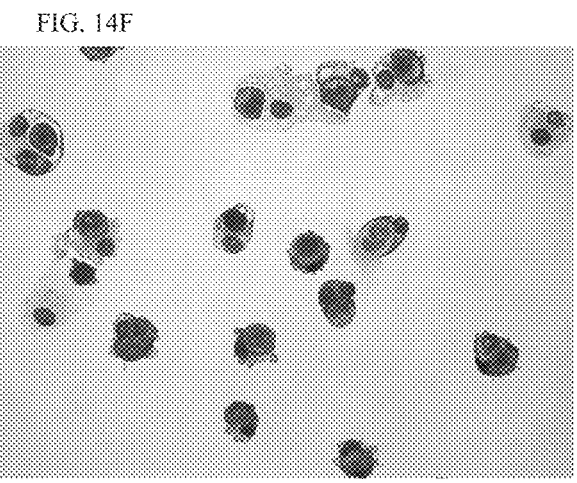

SEQUENCE LISTING

```
<160> NUMBER OF SEQ ID NOS: 48

<210> SEQ ID NO 1
<211> LENGTH: 118
<212> TYPE: PRT
<213> ORGANISM: Homo sapiens

<400> SEQUENCE: 1

Glu Glu Glu Leu Gln Val Ile Gln Pro Asp Lys Ser Val Ser Val Ala
1               5                   10                  15

Ala Gly Glu Ser Ala Ile Leu His Cys Thr Val Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Lys Glu Gly His Phe Pro Arg Val Thr Thr Val Ser
50                  55                  60

Glu Ser Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 2
<211> LENGTH: 504
<212> TYPE: PRT
<213> ORGANISM: Homo sapiens

<400> SEQUENCE: 2

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

Glu Leu Gln Val Ile Gln Pro Asp Lys Ser Val Leu Val Ala Ala Gly
        35                  40                  45

Glu Thr Ala Thr Leu Arg Cys Thr Ala Thr Ser Leu Ile Pro Val Gly
50                  55                  60
```

-continued

Pro Ile Gln Trp Phe Arg Gly Ala Gly Pro Gly Arg Glu Leu Ile Tyr
 65                  70                  75                  80

Asn Gln Lys Glu Gly His Phe Pro Arg Val Thr Thr Val Ser Asp Leu
                 85                  90                  95

Thr Lys Arg Asn Asn Met Asp Phe Ser Ile Arg Ile Gly Asn Ile Thr
                100                 105                 110

Pro Ala Asp Ala Gly Thr Tyr Tyr Cys Val Lys Phe Arg Lys Gly Ser
            115                 120                 125

Pro Asp Asp Val Glu Phe Lys Ser Gly Ala Gly Thr Glu Leu Ser Val
            130                 135                 140

Arg Ala Lys Pro Ser Ala Pro Val Val Ser Gly Pro Ala Ala Arg Ala
145                 150                 155                 160

Thr Pro Gln His Thr Val Ser Phe Thr Cys Glu Ser His Gly Phe Ser
                165                 170                 175

Pro Arg Asp Ile Thr Leu Lys Trp Phe Lys Asn Gly Asn Glu Leu Ser
            180                 185                 190

Asp Phe Gln Thr Asn Val Asp Pro Val Gly Glu Ser Val Ser Tyr Ser
            195                 200                 205

Ile His Ser Thr Ala Lys Val Val Leu Thr Arg Glu Asp Val His Ser
210                 215                 220

Gln Val Ile Cys Glu Val Ala His Val Thr Leu Gln Gly Asp Pro Leu
225                 230                 235                 240

Arg Gly Thr Ala Asn Leu Ser Glu Thr Ile Arg Val Pro Pro Thr Leu
                245                 250                 255

Glu Val Thr Gln Gln Pro Val Arg Ala Glu Asn Gln Val Asn Val Thr
                260                 265                 270

Cys Gln Val Arg Lys Phe Tyr Pro Gln Arg Leu Gln Leu Thr Trp Leu
            275                 280                 285

Glu Asn Gly Asn Val Ser Arg Thr Glu Thr Ala Ser Thr Val Thr Glu
            290                 295                 300

Asn Lys Asp Gly Thr Tyr Asn Trp Met Ser Trp Leu Leu Val Asn Val
305                 310                 315                 320

Ser Ala His Arg Asp Asp Val Lys Leu Thr Cys Gln Val Glu His Asp
                325                 330                 335

Gly Gln Pro Ala Val Ser Lys Ser His Asp Leu Lys Val Ser Ala His
            340                 345                 350

Pro Lys Glu Gln Gly Ser Asn Thr Ala Ala Glu Asn Thr Gly Ser Asn
            355                 360                 365

Glu Arg Asn Ile Tyr Ile Val Val Gly Val Val Cys Thr Leu Leu Val
            370                 375                 380

Ala Leu Leu Met Ala Ala Leu Tyr Leu Val Arg Ile Arg Gln Lys Lys
385                 390                 395                 400

Ala Gln Gly Ser Thr Ser Ser Thr Arg Leu His Glu Pro Glu Lys Asn
                405                 410                 415

Ala Arg Glu Ile Thr Gln Asp Thr Asn Asp Ile Thr Tyr Ala Asp Leu
            420                 425                 430

Asn Leu Pro Lys Gly Lys Lys Pro Ala Pro Gln Ala Ala Glu Pro Asn
            435                 440                 445

Asn His Thr Glu Tyr Ala Ser Ile Gln Thr Ser Pro Gln Pro Ala Ser
            450                 455                 460

Glu Asp Thr Leu Thr Tyr Ala Asp Leu Asp Met Val His Leu Asn Arg
465                 470                 475                 480

-continued

Thr Pro Lys Gln Pro Ala Pro Lys Pro Glu Pro Ser Phe Ser Glu Tyr
                485                 490                 495

Ala Ser Val Gln Val Pro Arg Lys
            500

<210> SEQ ID NO 3
<211> LENGTH: 118
<212> TYPE: PRT
<213> ORGANISM: Homo sapiens

<400> SEQUENCE: 3

Glu Glu Glu Leu Gln Val Ile Gln Pro Asp Lys Ser Val Ser Val Ala
1               5                   10                  15

Ala Gly Glu Ser Ala Ile Leu His Cys Thr Ile Thr Ser Leu Ile Pro
            20                  25                  30

Val Gly Pro Ile Gln Trp Phe Arg Gly Ala Gly Pro Ala Arg Glu Leu
        35                  40                  45

Ile Tyr Asn Gln Arg Glu Gly His Phe Pro Arg Val Thr Thr Val Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 4
<211> LENGTH: 118
<212> TYPE: PRT
<213> ORGANISM: Homo sapiens

<400> SEQUENCE: 4

Glu Glu Glu Val Gln Val Ile Gln Pro Asp Lys Ser Val Ser Val Ala
1               5                   10                  15

Ala Gly Glu Ser Ala Ile Leu His Cys Thr Leu Thr Ser Leu Ile Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly His Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 5
<211> LENGTH: 118
<212> TYPE: PRT
<213> ORGANISM: Homo sapiens

<400> SEQUENCE: 5

Glu Glu Glu Val Gln Ile Ile Gln Pro Asp Lys Ser Val Ser Val Ala

```
                1               5                  10                 15
        Ala Gly Glu Ser Val Ile Leu His Cys Thr Ile Thr Ser Leu Thr Pro
                        20                  25                 30

Val Gly Pro Ile Gln Trp Phe Arg Gly Ala Gly Pro Ala Arg Leu Leu
                        35                  40                 45

Ile Tyr Asn Gln Arg Glu Gly Pro Phe Pro Arg Val Thr Thr Val Ser
                        50                  55                 60

Glu Thr Thr Arg Arg Glu Asn Met Asp Phe Ser Ile Ser Ile Ser Asn
        65                      70                  75                 80

Ile Thr Pro Ala Asp Ala Gly Thr Tyr Tyr Cys Val Lys Leu Arg Lys
                            85                  90                 95

Gly Ser Pro Asp Thr Glu Phe Lys Ser Gly Ala Gly Thr Glu Leu Ser
                            100                 105                110

Val Arg Ala Lys Pro Ser
                            115

<210> SEQ ID NO 6
<211> LENGTH: 118
<212> TYPE: PRT
<213> ORGANISM: Homo sapiens

<400> SEQUENCE: 6

Glu Glu Glu Leu Gln Ile Ile Gln Pro Asp Lys Ser Val Ser Val Ala
        1               5                   10                 15

Ala Gly Glu Ser Ala Ile Leu His Cys Thr Ile Thr Ser Leu Ser Pro
                        20                  25                 30

Val Gly Pro Ile Gln Trp Phe Arg Gly Ala Gly Pro Ala Arg Val Leu
                        35                  40                 45

Ile Tyr Asn Gln Arg Gln Gly Pro Phe Pro Arg Val Thr Thr Val Ser
                        50                  55                 60

Glu Gly Thr Lys Arg Glu Asn Met Asp Phe Ser Ile Ser Ile Ser Asn
        65                      70                  75                 80

Ile Thr Pro Ala Asp Ala Gly Thr Tyr Tyr Cys Ile Lys Leu Arg Lys
                            85                  90                 95

Gly Ser Pro Asp Thr Glu Phe Lys Ser Gly Ala Gly Thr Glu Leu Ser
                            100                 105                110

Val Arg Ala Lys Pro Ser
                            115

<210> SEQ ID NO 7
<211> LENGTH: 118
<212> TYPE: PRT
<213> ORGANISM: Homo sapiens

<400> SEQUENCE: 7

Glu Glu Glu Ile Gln Val Ile Gln Pro Asp Lys Ser Val Ser Val Ala
        1               5                   10                 15

Ala Gly Glu Ser Val Ile Ile His Cys Thr Val Thr Ser Leu Phe Pro
                        20                  25                 30

Val Gly Pro Ile Gln Trp Phe Arg Gly Ala Gly Pro Ala Arg Val Leu
                        35                  40                 45

Ile Tyr Asn Gln Arg Gln Gly Arg Phe Pro Arg Val Thr Thr Val Ser
                        50                  55                 60

Glu Gly Thr Lys Arg Glu Asn Met Asp Phe Ser Ile Ser Ile Ser Asn
        65                      70                  75                 80

Ile Thr Pro Ala Asp Ala Gly Thr Tyr Tyr Cys Val Lys Val Arg Lys
```

85                  90                  95

Gly Ser Pro Asp Thr Glu Val Lys Ser Gly Ala Gly Thr Glu Leu Ser
            100                 105                 110

Val Arg Ala Lys Pro Ser
            115

<210> SEQ ID NO 8
<211> LENGTH: 118
<212> TYPE: PRT
<213> ORGANISM: Homo sapiens

<400> SEQUENCE: 8

Glu Glu Glu Val Gln Ile Ile Gln Pro Asp Lys Ser Val Ser Val Ala
1               5                   10                  15

Ala Gly Glu Ser Ile Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Glu Gly Arg Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Leu Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 9
<211> LENGTH: 118
<212> TYPE: PRT
<213> ORGANISM: Homo sapiens

<400> SEQUENCE: 9

Glu Glu Glu Val Gln Leu Ile Gln Pro Asp Lys Ser Val Ser Val Ala
1               5                   10                  15

Ala Gly Glu Ser Ala Ile Leu His Cys Thr Val Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Glu Gly Pro Phe Pro Arg Val Thr Thr Val Ser
    50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
            115

<210> SEQ ID NO 10
<211> LENGTH: 119
<212> TYPE: PRT
<213> ORGANISM: Homo sapiens

<400> SEQUENCE: 10

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
    50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser
        115

<210> SEQ ID NO 11
<211> LENGTH: 51
<212> TYPE: DNA
<213> ORGANISM: Homo sapiens

<400> SEQUENCE: 11
gaggaggagc tgcaggtgat tcagcctgac aagtccgtat cagttgcagc t        51

<210> SEQ ID NO 12
<211> LENGTH: 51
<212> TYPE: DNA
<213> ORGANISM: Homo sapiens

<400> SEQUENCE: 12
ggtcacagtg cagtgcagaa tggccgactc tccagctgca actgatacgg a         51

<210> SEQ ID NO 13
<211> LENGTH: 57
<212> TYPE: DNA
<213> ORGANISM: Homo sapiens
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t
<220> FEATURE:
<221> NAME/KEY: misc_feature
<222> LOCATION: (29)..(29)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 13
ctgcactgca ctgtgaccrs tnttnttcnt nttrstcnta tccagtggtt cagagga    57

<210> SEQ ID NO 14
<211> LENGTH: 48
<212> TYPE: DNA

<213> ORGANISM: Homo sapiens

<400> SEQUENCE: 14
attgtagatt aattcccggg ctggtccagc tcctctgaac cactggat    48

<210> SEQ ID NO 15
<211> LENGTH: 60
<212> TYPE: DNA
<213> ORGANISM: Homo sapiens

<400> SEQUENCE: 15
cgggaattaa tctacaatsa wargsawggc cacttccccc gggtaacaac tgtttcagag    60

<210> SEQ ID NO 16
<211> LENGTH: 63
<212> TYPE: DNA
<213> ORGANISM: Homo sapiens
<220> FEATURE:
<221> NAME/KEY: misc_feature
<222> LOCATION: (21)..(21)
<223> OTHER INFORMATION: n is a, c, g, or t

<400> SEQUENCE: 16
gttactgatg ctgatggaaa ngtccatgtt ttccytcyta syasyctctg aaacagttgt    60
tac    63

<210> SEQ ID NO 17
<211> LENGTH: 54
<212> TYPE: DNA
<213> ORGANISM: Homo sapiens

<400> SEQUENCE: 17
tccatcagca tcagtaacat caccccagca gatgccggca cctactactg tgtg    54

<210> SEQ ID NO 18
<211> LENGTH: 60
<212> TYPE: DNA
<213> ORGANISM: Homo sapiens
<220> FEATURE:
<221> NAME/KEY: misc_feature
<222> LOCATION: (32)..(41)
<223> OTHER INFORMATION: n = A,T,C or G

<400> SEQUENCE: 18
tccagactta aactccgtwt yaggasyasy cntccggaac ntcacacagt agtaggtgcc    60

<210> SEQ ID NO 19
<211> LENGTH: 54
<212> TYPE: DNA
<213> ORGANISM: Homo sapiens

<400> SEQUENCE: 19
acggagttta agtctggagc aggcactgag ctgtctgtgc gtgccaaacc ctct    54

<210> SEQ ID NO 20
<211> LENGTH: 63
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t -continued

<400> SEQUENCE: 20
ggatccgagg aggagnttca gnttattcag cctgacaagt ccgtatcagt tgcagctgga    60
gag                                                                  63

<210> SEQ ID NO 21
<211> LENGTH: 63
<212> TYPE: DNA
<213> ORGANISM: Homo sapiens
<220> FEATURE:
<221> NAME/KEY: misc_feature
<222> LOCATION: (27)..(27)
<223> OTHER INFORMATION: n is a, c, g, or t

<400> SEQUENCE: 21 gggcccaca gggatcaggg aggtaanagt gcagtgcaga atggccgact ctccagctgc     60
aac                                                                  63

<210> SEQ ID NO 22
<211> LENGTH: 54
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 22
ctgatccctg tggggcccnt tcagtggntt agaggagctg gaccagcccg ggaa          54

<210> SEQ ID NO 23
<211> LENGTH: 45
<212> TYPE: DNA
<213> ORGANISM: Homo sapiens
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 23
gtggccttct ttttgattaa naanaanttc ccgggctggt ccagc                    45

<210> SEQ ID NO 24
<211> LENGTH: 63
<212> TYPE: DNA
<213> ORGANISM: Homo sapiens
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (28)..(28)
<223> OTHER INFORMATION: n is a, c, g, or t

<400> SEQUENCE: 24
aatcaaaaag aaggccacnt tccccggntt acaactgttt cagagtccac aaagagagaa    60
aac                                                                 63

<210> SEQ ID NO 25
<211> LENGTH: 66
<212> TYPE: DNA
<213> ORGANISM: Homo sapiens
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t

<400> SEQUENCE: 25
gccggcatct gctggggtga tgttactgat gctaanggaa angtcaangt tttctctctt    60
tgtgga                                                              66

<210> SEQ ID NO 26
<211> LENGTH: 63
<212> TYPE: DNA
<213> ORGANISM: Homo sapiens
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t

<400> SEQUENCE: 26
accccagcag atgccggcac ctactactgt nttaagnttc ggaaagggag ccctgacacg    60
gag                                                                 63

<210> SEQ ID NO 27
<211> LENGTH: 66
<212> TYPE: DNA
<213> ORGANISM: Homo sapiens
<220> FEATURE:
<221> NAME/KEY: misc_feature
<222> LOCATION: (48)..(48)
<223> OTHER INFORMATION: n is a, c, g, or t

<400> SEQUENCE: 27
agagggtttg gcacgcacag acagctcagt gcctgctcca gacttaanct ccgtgtcagg    60
gctccc                                                              66

<210> SEQ ID NO 28
<211> LENGTH: 47
<212> TYPE: DNA
<213> ORGANISM: Homo sapiens
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 28

-continued ggatccgagg aggagnttca gnttattcag cctgacaagt ccgtatc    47

<210> SEQ ID NO 29
<211> LENGTH: 58
<212> TYPE: DNA
<213> ORGANISM: Homo sapiens

<400> SEQUENCE: 29
gtgcagtgca gaatggccga ctctccagct gcaactgata cggacttgtc aggctgaa    58

<210> SEQ ID NO 30
<211> LENGTH: 49
<212> TYPE: DNA
<213> ORGANISM: Homo sapiens
<220> FEATURE:
<221> NAME/KEY: misc_feature
<222> LOCATION: (17)..(17)
<223> OTHER INFORMATION: n is a, c, g, or t

<400> SEQUENCE: 30
cattctgcac tgcactntta cctccctgwy tcctgtgggg cccatccag    49

<210> SEQ ID NO 31
<211> LENGTH: 44
<212> TYPE: DNA
<213> ORGANISM: Homo sapiens

<400> SEQUENCE: 31
cgggctggtc cagctcctct gaaccactgg atgggcccca cagg    44

<210> SEQ ID NO 32
<211> LENGTH: 74
<212> TYPE: DNA
<213> ORGANISM: Homo sapiens
<220> FEATURE:
<221> NAME/KEY: misc_feature
<222> LOCATION: (46)..(46)
<223> OTHER INFORMATION: n is a, c, g, or t

<400> SEQUENCE: 32
gagctggacc agcccggswa ttaatctaca atcaaargsa kggccntttc ccccgggtaa    60
caactgtttc agag    74

<210> SEQ ID NO 33
<211> LENGTH: 47
<212> TYPE: DNA
<213> ORGANISM: Homo sapiens

<400> SEQUENCE: 33
gaaaagtcca tgttttctct cyttgtasyc tctgaaacag ttgttac    47

<210> SEQ ID NO 34
<211> LENGTH: 59
<212> TYPE: DNA
<213> ORGANISM: Homo sapiens

<400> SEQUENCE: 34
agagaaaaca tggactttc catcagcatc agtaacatca ccccagcaga tgccggcac    59

<210> SEQ ID NO 35
<211> LENGTH: 59
<212> TYPE: DNA
<213> ORGANISM: Homo sapiens
<220> FEATURE:

```
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 35
ctccgtgtca gggctccctt tccgaanctt aanacagtag taggtgccgg catctgctg    59

<210> SEQ ID NO 36
<211> LENGTH: 64
<212> TYPE: DNA
<213> ORGANISM: Homo sapiens
<220> FEATURE:
<221> NAME/KEY: misc_feature
<222> LOCATION: (17)..(17)
<223> OTHER INFORMATION: n is a, c, g, or t

<400> SEQUENCE: 36
gagccctgac acggagntta agtctggagc aggcactgag ctgtctgtgc gtgccaaacc   60
ctct                                                               64

<210> SEQ ID NO 37
<211> LENGTH: 118
<212> TYPE: PRT
<213> ORGANISM: Homo sapiens

<400> SEQUENCE: 37

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Leu Leu
        35                  40                  45

Ile Tyr Asn Gln Arg Gln Gly Pro Phe Pro Arg Val Thr Thr Val Ser
    50                  55                  60

Glu Thr Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
        115

<210> SEQ ID NO 38
<211> LENGTH: 118
<212> TYPE: PRT
<213> ORGANISM: Homo sapiens

<400> SEQUENCE: 38

Glu Glu Glu Val Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Lys Gln Gly Pro Phe Pro Arg Val Thr Thr Ile Ser
    50                  55                  60
```

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser
            115

<210> SEQ ID NO 39
<211> LENGTH: 118
<212> TYPE: PRT
<213> ORGANISM: Homo sapiens

<400> SEQUENCE: 39

Glu Glu Glu Leu Gln Ile Ile Gln Pro Asp Lys Ser Val Ser Val Ala
1               5                   10                  15

Ala Gly Glu Ser Ala Ile Leu His Cys Thr Ile Thr Ser Leu Thr Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Val Ser
    50                  55                  60

Glu Gly Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Val Lys Ser Gly Ala Gly Thr Glu Leu Ser
            100                 105                 110

Val Arg Ala Lys Pro Ser
            115

<210> SEQ ID NO 40
<211> LENGTH: 345
<212> TYPE: PRT
<213> ORGANISM: Homo sapiens

<400> SEQUENCE: 40

Glu Glu Glu Val Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Ile Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Ala Pro Cys Pro Cys Pro
            115                 120                 125

Ala Pro Glu Phe Leu Gly Gly Pro Ser Val Phe Leu Phe Pro Pro Lys
130                 135                 140

Pro Lys Asp Thr Leu Met Ile Ser Arg Thr Pro Glu Val Thr Cys Val
145                 150                 155                 160

Val Val Asp Val Ser Gln Glu Asp Pro Glu Val Gln Phe Asn Trp Tyr
            165                 170                 175

Val Asp Gly Val Glu Val His Asn Ala Lys Thr Lys Pro Arg Glu Glu
            180                 185                 190

Gln Phe Asn Ser Thr Tyr Arg Val Val Ser Val Leu Thr Val Leu His
            195                 200                 205

Gln Asp Trp Leu Asn Gly Lys Glu Tyr Lys Cys Lys Val Ser Asn Lys
        210                 215                 220

Gly Leu Pro Ser Ser Ile Glu Lys Thr Ile Ser Lys Ala Lys Gly Gln
225                 230                 235                 240

Pro Arg Glu Pro Gln Val Tyr Thr Leu Pro Pro Ser Gln Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
            275                 280                 285

Tyr Lys Thr Thr Pro Pro Val Leu Asp Ser Asp Gly Ser Phe Phe Leu
        290                 295                 300

Tyr Ser Arg Leu Thr Val Asp Lys Ser Arg Trp Gln Glu Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 41
<211> LENGTH: 346
<212> TYPE: PRT
<213> ORGANISM: Homo sapiens

<400> SEQUENCE: 41

Glu Glu Glu Leu Gln Ile Ile Gln Pro Asp Lys Ser Val Leu Val Ala
1               5                   10                  15

Ala Gly Glu Thr Ala Thr Leu Arg Cys Thr Ile Thr Ser Leu Phe Pro
            20                  25                  30

Val Gly Pro Ile Gln Trp Phe Arg Gly Ala Gly Pro Gly Arg Val Leu
        35                  40                  45

Ile Tyr Asn Gln Arg Gln Gly Pro Phe Pro Arg Val Thr Thr Val Ser
50                  55                  60

Asp Thr Thr Lys Arg Asn Asn Met Asp Phe Ser Ile Arg Ile Gly Asn
65                  70                  75                  80

Ile Thr Pro Ala Asp Ala Gly Thr Tyr Tyr Cys Ile Lys Phe Arg Lys
                85                  90                  95

Gly Ser Pro Asp Asp Val Glu Phe Lys Ser Gly Ala Gly Thr Glu Leu
            100                 105                 110

Ser Val Arg Ala Lys Pro Ser Ala Ala Pro Pro Cys Pro Pro Cys
        115                 120                 125

Pro Ala Pro Glu Phe Leu Gly Gly Pro Ser Val Phe Leu Phe Pro Pro
    130                 135                 140

Lys Pro Lys Asp Thr Leu Met Ile Ser Arg Thr Pro Glu Val Thr Cys
145                 150                 155                 160

Val Val Val Asp Val Ser Gln Glu Asp Pro Glu Val Gln Phe Asn Trp

```
            165                 170                 175
Tyr Val Asp Gly Val Glu Val His Asn Ala Lys Thr Lys Pro Arg Glu
            180                 185                 190

Glu Gln Phe Asn Ser Thr Tyr Arg Val Val Ser Val Leu Thr Val Leu
            195                 200                 205

His Gln Asp Trp Leu Asn Gly Lys Glu Tyr Lys Cys Lys Val Ser Asn
            210                 215                 220

Lys Gly Leu Pro Ser Ser Ile Glu Lys Thr Ile Ser Lys Ala Lys Gly
225                 230                 235                 240

Gln Pro Arg Glu Pro Gln Val Tyr Thr Leu Pro Pro Ser Gln Glu Glu
            245                 250                 255

Met Thr Lys Asn Gln Val Ser Leu Thr Cys Leu Val Lys Gly Phe Tyr
            260                 265                 270

Pro Ser Asp Ile Ala Val Glu Trp Glu Ser Asn Gly Gln Pro Glu Asn
            275                 280                 285

Asn Tyr Lys Thr Thr Pro Pro Val Leu Asp Ser Asp Gly Ser Phe Phe
            290                 295                 300

Leu Tyr Ser Arg Leu Thr Val Asp Lys Ser Arg Trp Gln Glu Gly Asn
305                 310                 315                 320

Val Phe Ser Cys Ser Val Met His Glu Ala Leu His Asn His Tyr Thr
                325                 330                 335

Gln Lys Ser Leu Ser Leu Ser Pro Gly Lys
            340                 345

<210> SEQ ID NO 42
<211> LENGTH: 344
<212> TYPE: PRT
<213> ORGANISM: Homo sapiens

<400> SEQUENCE: 42

Glu Glu Glu Val Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
        35                  40                  45

Ile Tyr Asn Gln Arg Gln Gly Pro Phe Pro Arg Val Thr Thr Ile Ser
    50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Ala Val Glu Cys Pro Pro Cys Pro
        115                 120                 125

Ala Pro Pro Val Ala Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Gln Phe Asn Trp Tyr Val
                165                 170                 175

Asp Gly Met Glu Val His Asn Ala Lys Thr Lys Pro Arg Glu Glu Gln
            180                 185                 190
```

```
Phe Asn Ser Thr Phe Arg Val Val Ser Val Leu Thr Val His Gln
            195                 200                 205
Asp Trp Leu Asn Gly Lys Glu Tyr Lys Cys Lys Val Ser Asn Lys Gly
210                 215                 220
Leu Pro Ala Pro Ile Glu Lys Thr Ile Ser Lys Thr Lys Gly Gln Pro
225                 230                 235                 240
Arg Glu Pro Gln Val Tyr Thr Leu Pro Pro Ser Arg Glu Glu Met Thr
            245                 250                 255
Lys Asn Gln Val Ser Leu Thr Cys Leu Val Lys Gly Phe Tyr Pro Ser
            260                 265                 270
Asp Ile Ala Val Glu Trp Glu Ser Asn Gly Gln Pro Glu Asn Asn Tyr
            275                 280                 285
Lys Thr Thr Pro Pro Met Leu Asp Ser Asp Gly Ser Phe Phe Leu Tyr
290                 295                 300
Ser Lys Leu Thr Val Asp Lys Ser Arg Trp Gln Gln Gly Asn Val Phe
305                 310                 315                 320
Ser Cys Ser Val Met His Glu Ala Leu His Asn His Tyr Thr Gln Lys
            325                 330                 335
Ser Leu Ser Leu Ser Pro Gly Lys
            340

<210> SEQ ID NO 43
<211> LENGTH: 345
<212> TYPE: PRT
<213> ORGANISM: Homo sapiens

<400> SEQUENCE: 43

Glu Glu Glu Leu Gln Ile Ile Gln Pro Asp Lys Ser Val Leu Val Ala
1               5                   10                  15
Ala Gly Glu Thr Ala Thr Leu Arg Cys Thr Ile Thr Ser Leu Phe Pro
            20                  25                  30
Val Gly Pro Ile Gln Trp Phe Arg Gly Ala Gly Pro Gly Arg Val Leu
        35                  40                  45
Ile Tyr Asn Gln Arg Gln Gly Pro Phe Pro Arg Val Thr Thr Val Ser
    50                  55                  60
Asp Thr Thr Lys Arg Asn Asn Met Asp Phe Ser Ile Arg Ile Gly Asn
65                  70                  75                  80
Ile Thr Pro Ala Asp Ala Gly Thr Tyr Tyr Cys Ile Lys Phe Arg Lys
                85                  90                  95
Gly Ser Pro Asp Asp Val Glu Phe Lys Ser Gly Ala Gly Thr Glu Leu
            100                 105                 110
Ser Val Arg Ala Lys Pro Ser Ala Ala Ala Val Glu Cys Pro Pro Cys
        115                 120                 125
Pro Ala Pro Pro Val Ala Gly Pro Ser Val Phe Leu Phe Pro Pro Lys
    130                 135                 140
Pro Lys Asp Thr Leu Met Ile Ser Arg Thr Pro Glu Val Thr Cys Val
145                 150                 155                 160
Val Val Asp Val Ser His Glu Asp Pro Glu Val Gln Phe Asn Trp Tyr
                165                 170                 175
Val Asp Gly Met Glu Val His Asn Ala Lys Thr Lys Pro Arg Glu Glu
            180                 185                 190
Gln Phe Asn Ser Thr Phe Arg Val Val Ser Val Leu Thr Val Val His
        195                 200                 205
Gln Asp Trp Leu Asn Gly Lys Glu Tyr Lys Cys Lys Val Ser Asn Lys
    210                 215                 220
```

Gly Leu Pro Ala Pro Ile Glu Lys Thr Ile Ser Lys Thr Lys Gly Gln
225                 230                 235                 240

Pro Arg Glu Pro Gln Val Tyr Thr Leu Pro Pro Ser Arg Glu Glu Met
            245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
            275                 280                 285

Tyr Lys Thr Thr Pro Pro Met Leu Asp Ser Asp Gly Ser Phe Phe Leu
            290                 295                 300

Tyr Ser Lys Leu Thr Val Asp Lys Ser Arg Trp Gln Gln Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Pro Gly Lys
            340                 345

<210> SEQ ID NO 44
<211> LENGTH: 158
<212> TYPE: PRT
<213> ORGANISM: Homo sapiens

<400> SEQUENCE: 44

Glu Glu Glu Val Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
            35                  40                  45

Ile Tyr Asn Gln Arg Gln Gly Pro Phe Pro Arg Val Thr Thr Ile Ser
        50                  55                  60

Glu Thr Thr Arg Arg Glu Asn Met Asp Phe Ser Ile Ser Ile Ser Asn
65                  70                  75                  80

Ile Thr Pro Ala Asp Ala Gly Thr Tyr Tyr Cys Ile Lys Phe Arg Lys
                85                  90                  95

Gly Ser Pro Asp Thr Glu Phe Lys Ser Gly Ala Gly Thr Glu Leu Ser
            100                 105                 110

Val Arg Ala Lys Pro Ser Ala Ala Ala Arg Met Lys Gln Leu Glu Asp
            115                 120                 125

Lys Val Glu Glu Leu Leu Ser Lys Asn Tyr His Leu Glu Asn Glu Val
            130                 135                 140

Ala Arg Leu Lys Lys Leu Val Gly Ala Ala Ser Gly Ala Asp
145                 150                 155

<210> SEQ ID NO 45
<211> LENGTH: 246
<212> TYPE: PRT
<213> ORGANISM: Homo sapiens

<400> SEQUENCE: 45

Glu Glu Glu Val Gln Ile Ile Gln Pro Asp Lys Ser Val Ser Val Ala
1               5                   10                  15

Ala Gly Glu Ser Ala Ile Leu His Cys Thr Ile Thr Ser Leu Phe Pro
            20                  25                  30

Val Gly Pro Ile Gln Trp Phe Arg Gly Ala Gly Pro Ala Arg Val Leu
            35                  40                  45

```
Ile Tyr Asn Gln Arg Gln Gly Pro Phe Pro Arg Val Thr Thr Ile Ser
 50                  55                  60

Glu Thr Thr Arg Arg Glu Asn Met Asp Phe Ser Ile Ser Ile Ser Asn
 65                  70                  75                  80

Ile Thr Pro Ala Asp Ala Gly Thr Tyr Tyr Cys Ile Lys Phe Arg Lys
                 85                  90                  95

Gly Ser Pro Asp Thr Glu Phe Lys Ser Gly Ala Gly Thr Glu Leu Ser
                100                 105                 110

Val Arg Ala Lys Pro Ser Gly Gly Gly Ser Gly Gly Gly Gly Ser
                115                 120                 125

Glu Glu Glu Val Gln Ile Ile Gln Pro Asp Lys Ser Val Ser Val Ala
                130                 135                 140

Ala Gly Glu Ser Ala Ile Leu His Cys Thr Ile Thr Ser Leu Phe Pro
145                 150                 155                 160

Val Gly Pro Ile Gln Trp Phe Arg Gly Ala Gly Pro Ala Arg Val Leu
                165                 170                 175

Ile Tyr Asn Gln Arg Gln Gly Pro Phe Pro Arg Val Thr Thr Ile Ser
                180                 185                 190

Glu Thr Thr Arg Arg Glu Asn Met Asp Phe Ser Ile Ser Ile Ser Asn
                195                 200                 205

Ile Thr Pro Ala Asp Ala Gly Thr Tyr Tyr Cys Ile Lys Phe Arg Lys
                210                 215                 220

Gly Ser Pro Asp Thr Glu Phe Lys Ser Gly Ala Gly Thr Glu Leu Ser
225                 230                 235                 240

Val Arg Ala Lys Pro Ser
                245

<210> SEQ ID NO 46
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 46

Leu Asn Asp Ile Phe Glu Ala Gln Lys Ile Glu Trp His Glu
1               5                  10

<210> SEQ ID NO 47
<211> LENGTH: 118
<212> TYPE: PRT
<213> ORGANISM: Homo sapiens

<400> SEQUENCE: 47

Glu Glu Glu Ile Gln Val Ile Gln Pro Asp Lys Ser Val Ser Val Ala
1               5                  10                  15

Ala Gly Glu Ser Val Ile Leu His Cys Thr Ile Thr Ser Leu Phe Pro
                20                  25                  30

Val Gly Pro Ile Gln Trp Phe Arg Gly Ala Gly Pro Ala Arg Val Leu
                35                  40                  45

Ile Tyr Asn Gln Arg Gln Gly Arg Phe Pro Arg Val Thr Thr Val Ser
 50                  55                  60

Glu Gly Thr Lys Arg Glu Asn Met Asp Phe Ser Ile Ser Ile Ser Asn
65                  70                  75                  80

Ile Thr Pro Ala Asp Ala Gly Thr Tyr Tyr Cys Val Lys Val Arg Lys
                85                  90                  95
```

```
Gly Ser Pro Asp Thr Glu Val Lys Ser Gly Ala Gly Thr Glu Leu Ser
            100                 105                 110

Val Arg Ala Lys Pro Ser
        115

<210> SEQ ID NO 48
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 48

Gly Leu Asn Asp Ile Phe Glu Ala Gln Lys Ile Glu Trp His Glu
1               5                   10                  15
```

HIGH AFFINITY SIRP-ALPHA REAGENTS AND METHODS OF USING

CROSS REFERENCE

This application claims benefit and is a Continuation of application Ser. No. 15/912,471, filed Mar. 5, 2018, which claims the benefit of application Ser. No. 14/371,370 filed Jul. 9, 2014, now U.S. Pat. No. 9,944,911, issued Apr. 17, 2018, which is a 371 application and claims the benefit of PCT Application No. PCT/US2013/021937, filed Jan. 17, 2013, which claims benefit of U.S. Provisional Patent Application No. 61/587,247, filed Jan. 17, 2012, which applications are incorporated herein by reference in their entirety.

GOVERNMENT RIGHTS

This invention was made with Government support under contracts CA086017, HL058770, and CA139490 awarded by the National Institutes of Health. The Government has certain rights in the invention.

INCORPORATION BY REFERENCE OF SEQUENCE LISTING PROVIDED AS A TEXT FILE

A Sequence Listing is provided herewith in a text file, S11-263_STAN-868CON2_SEQLIST, created on Jan. 17, 2021 and having a size of 4100 41661 bytes. The contents of the text file are incorporated herein by reference in its entirety.

BACKGROUND OF THE INVENTION

Turnover of cells begins with the induction of an apoptotic program or other cellular changes that mark them for removal, and the subsequent recognition of markers by phagocytes, including macrophages, dendritic cells, and the like. This process requires a specific and selective removal of unwanted cells. Discrimination of the healthy from the unwanted/aged/dying cells display markers or ligands called "eat-me" signals, i.e. "altered self", which can in turn be recognized by receptors on the phagocytes. Healthy cells may display "don't eat-me" signals that actively inhibit phagocytosis; these signals are either downregulated in the dying cells or present in an altered conformation. The cell surface protein CD47 on healthy cells and its engagement of a phagocyte receptor, SIRPα, constitutes a key "don't eat-me" signal that can turn off engulfment mediated by multiple modalities, including apoptotic cell clearance and FcR mediated phagocytosis. Blocking the CD47 mediated engagement of SIRPα on a phagocyte, or the loss of CD47 expression in knockout mice, can cause removal of live cells and non-aged erythrocytes. Alternatively, blocking SIRPα recognition also allows engulfment of targets that are not normally phagocytosed.

CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2007) J.B.C. 282:14567-75; and the role of SIRPα cis dimerization in CD47 binding is discussed by Lee et al. (2010) J.B.C. 285:37953-63.

In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo. CD47 is also constitutively upregulated on a number of cancers. Overexpression of CD47 by tumor cells may increase pathogenicity by allowing the cell to evade phagocytosis.

SUMMARY OF THE INVENTION

High affinity SIRPα polypeptides and analogs thereof are provided, which are referred to herein as high affinity SIRPα reagents. The reagents are sequence variants of the native human SIRPα protein, and have utility for in vivo and in vitro methods that block the interaction between native SIRPα protein and its receptor, CD47. The amino acid changes that provide for increased affinity are localized in the d1 domain, and thus the high affinity SIRPα reagents of the invention comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc.

In one embodiment, the invention provides soluble high affinity SIRPα reagents, which lack the SIRPα transmembrane domain, and comprise at least one amino acid change in the d1 domain relative to wild-type human SIRPα, which amino acid change increases the affinity of the SIRPα polypeptide binding to CD47. The high affinity SIRPα polypeptide may be post-translationally modified, for example by glycosylation, pegylation, etc. In some embodiments, the high affinity SIRPα reagent is a fusion protein comprising an Fc domain.

The invention also includes pharmaceutical formulations of high affinity SIRPα reagents in combination with a pharmaceutically acceptable excipient. Such formulations may be provided as a unit dose, e.g. a dose effective to increase targeted phagocytosis in an individual. Pharmaceutical formulations also include lyophilized or other preparations of the high affinity SIRPα reagents, which may be reconstituted for use.

In some embodiments, methods are provided to manipulate targeted phagocytosis of cells, e.g. by macrophages or other mammalian phagocytic cells. In such methods, a cell expressing CD47 is contacted with a high affinity SIRPα reagent of the invention in a dose effective to block the interaction between endogenous SIRPα and CD47. Blocking this interaction allows engulfment of targets that are not normally phagocytosed. The contacting may be performed in vivo, e.g. for therapeutic purposes, and in vitro, e.g. for screening assays and the like. The high affinity SIRPα reagent for these purposes may be multimeric; or monomeric. Monomeric reagents find particular use for administration in combination with an antibody that selectively binds to the cell targeted for phagocytosis.

In related embodiments, tumor cells, e.g. solid tumors such as carcinomas, sarcomas, melanomas, etc.; leukemias; lymphomas, etc. are targeted for phagocytosis by contacting the tumor cell with a dose of a high affinity SIRPα polypeptide that is effective to block, or mask CD47 on the cell surface, allowing engulfment of targets that are not normally phagocytosed. Administration of an effective dose of high affinity SIRPα polypeptide to a patient prevents interaction between CD47 and SIRPα, which increases the clearance of tumor cells via phagocytosis. For these purposes it can be advantageous to administer a high affinity SIRPα variant in the presence of an immunoglobulin Fc bound to the cell targeted for phagocytosis, which provides a pro-phagocytic signal. In these aspects, the high affinity SIRPα polypeptide can be combined with monoclonal antibodies directed against one or more additional tumor cell markers, which compositions can be synergistic in enhancing phagocytosis and elimination of tumor cells as compared to the use of single agents. Monomeric high affinity SIRPα reagents are advantageous for this purpose as they have low red blood cell toxicity. Alternatively a SIRPα fusion construct comprising an immunoglobulin Fc region, e.g. one that provides a pro-phagocytic signal, may be administered.

In other embodiments the high affinity SIRPα reagent comprises a detectable label. Such a labeled reagent can be used for imaging purposes in vitro or in vivo, e.g. in the imaging of a tumor.

BRIEF DESCRIPTION OF THE DRAWINGS

FIG. 1A-1E. Directed evolution of high-affinity SIRPα variants. (FIG. 1A). Schematic of CD47 blockade by soluble high-affinity SIRPα. (Left) In the basal state, CD47 expression on cancer cells activates SIRPα on macrophages, initiating an inhibitory cascade through SHP 1 and 2 tyrosine phosphatases and preventing cancer cell phagocytosis. (Right) Soluble, high-affinity SIRPα protein competitively antagonizes CD47 and prevents engagement with SIRPα on macrophages, thereby disinhibiting phagocytosis. (FIG. 1B). Schematic representation of yeast surface-display of the SIRPα V-set Ig domain (domain 1, d1). Yeast clones (grey cells) present different variants of SIRPα (colored bumps). Inset indicates the linkage of SIRPα to the yeast cell surface via fusion with Aga2 and selection with biotinylated CD47. (FIG. 1C). Summary of sequences and SPR affinity measurements of engineered SIRPα variants. The position of the mutated residues and their corresponding sequence in wild-type allele 1 is denoted at the top of the table. Bold text indicates the consensus mutations and shading indicates contact residues in the consensus. Representative SPR sensorgrams of wild-type SIRPα and high-affinity variant FD6 binding immobilized CD47 are shown to the right. RU=response units. (FIG. 1D). The crystal structure of the FD6:CD47 complex depicted as transparent surfaces containing ribbon representations of FD6 and CD47. (FIG. 1E). Superimposition of the wild-type and high-affinity SIRPα:CD47 complexes. Insets show mutated contact residues in the SIRPα C'D loop (sticks) and the binding interface of CD47 (top, space fill; bottom, sticks).

(FIG. 2A). Dose-response curves of CD47 antagonism on Raji lymphoma cells with wild-type SIRPα allele 1 (WTa1), anti-CD47 clone B6H12 Fab fragments, or two high-affinity SIRPα variants (FD6, CV1). Cells stained with titrating concentrations of CD47 blocking agents in competition with 100 nM Alexa Fluor 647-conjugated WT SIRPα tetramer. (FIG. 2B). Representative images of phagocytosis assays performed with CFSE-labeled Raji lymphoma cells and RFP+ macrophages with vehicle control (PBS) or a high-affinity SIRPα mutant fused to human IgG4 (CV1-hIgG4). Insets show macrophage that has ingested multiple cancer cells. Scale bar=50 μm. (FIG. 2C). Representative plots showing phagocytosis assays analyzed by flow cytometry. Human macrophages were co-cultured with GFP+ DLD-1 cells and the indicated treatments. Gates were used to evaluate GFP+ macrophages as a percentage of the total macrophage population. (FIG. 2D). Phagocytosis of GFP+ tumor cells by donor-derived human macrophages as assessed by flow cytometry. All protein treatments used at 100 nM. The percentage of GFP+ macrophages was normalized to the maximal response by each donor against each cell line. (FIG. 2E). Phagocytosis of GFP+ DLD-1 cells with varying concentrations of SIRPα-Fc variants or an isotype-matched anti-CD47 antibody (clone B6H12). (FIG. 2F). Phagocytosis of GFP+ DLD-1 cells with non-specific isotype control (mIgG1), non-blocking anti-CD47 (2D3), or anti-EpCam antibodies. All antibodies were used at 20 μg/mL. WT SIRPα or high-affinity SIRPα variant FD6 monomers were used at 1 μM and combined as indicated. (FIG. 2G). Phagocytosis of GFP+ DLD-1 cells with varying concentrations of cetuximab (anti-EGFR) alone or in combination with WT SIRPα monomer or high affinity SIRPα monomers. All SIRPα variants used at 100 nM. (FIG. 2H). Phagocytosis of GFP+ Raji cells with varying concentrations of rituximab (anti-CD20) alone or in the presence of WT SIRPα monomer or high-affinity SIRPα monomers. All SIRPα variants were used at 100 nM. D-H All human macrophage phagocytosis assays were performed with macrophages derived from a minimum of three independent blood donors. Error bars indicate standard deviation. ns=not significant, *p<0.05, p<0.01, *p<0.001 versus WT SIRPα variants (FIG. 2D, 2G, 2H), versus B6H12-hIgG4 (e), or as otherwise indicated.

(FIG. 3A). Representative image of GFP-luciferase+ DLD-1 cells engrafted into the peritoneal cavity, forming disseminated tumor nodules amongst surrounding bowel loops. (FIG. 3B). Survival of mice engrafted with GFP-luciferase+ DLD-1 cells upon treatment with vehicle control (PBS) or high-affinity SIRPα-hIgG4 fusion protein (CV1-hIgG4). (FIG. 3C). Representative analysis of human Fc bound to the surface of whole blood cells from animals treated in b. (FIG. 3D). Blood analysis of treated animals in b showing mean and standard deviation from four animals per cohort over time. Dotted line shows lower limit of normal values. (FIG. 3E). Growth of GFP-luciferase+ 639-V bladder cancer cells in the dorsal subcutaneous tissue of NSG mice upon treatment with the indicated therapies as evaluated by bioluminescence imaging. Bars depict median values, points show values from individual mice. (FIG. 3F). Representative bioluminescence images of 639-V engrafted mice from each treatment group on day 37 post-engraftment. (FIG. 3G). Tumor volumes of 639-V engrafted mice on day 38 post-engraftment. Bars depict median values, points show values from individual mice. (FIG. 3H). Survival of mice engrafted with GFP-luciferase+ 639-V cells. (FIG. 3A-3H). Black arrows mark the start and stop of daily treatment. ns=not significant, *p<0.05, p<0.01, *p<0.001 for vehicle control treatment versus CV1-hIgG4.

FIG. 4A-4F. High-affinity SIRPα monomers enhance the efficacy of monoclonal antibodies in vivo. (FIG. 4A). Growth of GFP-luciferase+ Raji lymphoma tumors upon daily treatment with PBS, CV1 monomer, rituximab, or rituximab plus CV1 monomer, as evaluated by bioluminescence imaging. Bars indicate median values, points indicate values from individual mice. (FIG. 4B). Representative bioluminescence images of mice on day 29 post-engraftment. Circles indicate sites of primary tumors, arrow indicates site of metastases to axillary lymph nodes. (FIG. 4C). Mean tumor volume measurements of mice from (FIG. 4A). Error bars depict standard deviation. (FIG. 4D). Survival of lymphoma-bearing mice from (FIG. 4A). (FIG. 4E). Growth of GFP-luciferase+ Raji lymphoma tumors upon bi-weekly treatment with PBS, CV1 monomer, alemtuzumab, or alemtuzumab plus CV1 monomer, as evaluated by tumor volume measurements. Bars indicate median values, points indicate values from individual mice. F. Survival of lymphoma-bearing mice from (FIG. 4E). (FIG. 4A-4F) Black arrows indicate the start and stop of treatment. ns=not significant, $*p<0.05$, $p<0.01$, $*p<0.001$ for all groups versus rituximab+CV1 monomer, or alemtuzumab alone versus alemtuzumab+CV1 monomer.

(FIG. 5A). Left: Table of randomized positions of the 'contact residue' library with possible amino acid variants and the location of the randomized positions within SIRPα. Right: Location and description of the randomized positions for the non-contact, 'core residue' library. SIRPα is depicted and CD47 is depicted, and the randomized positions are represented as space filling side chains. (FIG. 5B). Summary of sequences of SIRPα variants obtained after the first generation of selections. The position of the mutated residues and their corresponding sequence in wild-type allele 1 is denoted at the top of the table. Shading indicates 'contact' mutations occurring at the SIRPα:CD47 interface. Italic font indicates mutations at positions that were not randomized in the pooled library (Glu47 and His56).

(FIG. 8A). Titration curves of wild-type SIRPα allele 1 monomer (WTa1 mono), wild type SIRPα allele 1 tetramer (WTa1 tetramer), or high-affinity SIRPα variants (FD6, FA4) binding to Jurkat leukemia cells. Error bars indicate standard deviation. (FIG. 8B). CD47 blocking assay on Jurkat cells. CD47 antagonists were added in competition with Alexa Fluor 647-conjugated wild-type SIRPα tetramer. Blocking was tested with a first generation SIRPα mutant as a monomer (1A5 mono), a second generation SIRPα mutant as a monomer (FD6 mono), a second generation SIRPα mutant as an Fc fusion with human IgG4 (FD6-hIgG4), and anti-CD47 clone B6H12. Error bars indicate standard deviation. (FIG. 8C). Binding of wild-type SIRPα-Fc proteins (WTa1-hIgG4, WTa2-hIgG4), high-affinity SIRPα-Fc proteins (FD-hIgG4, CV1-hIgG4), and anti-CD47 antibody clone B6H12 (B6H12-hIgG4) to DLD-1 colon cancer cells.

FIG. 10A-10D. Treatment with high-affinity SIRPα-Fc variants causes macrophage infiltration and affects red cell indices. (FIG. 10A). Dissected palpable subcutaneous tissue mass from a CV1-hIgG4 treated mouse. Left=white light, right=GFP fluorescence. Dashed ovals encircle two superficial tumor nodules, asterisks mark macrophage-rich stromal infiltrate. Scale bar=5 mm. (FIG. 10B). Hematoxylin and eosin staining of palpable subcutaneous tissue mass from a CV1-hIgG4 treated mouse, demonstrating the presence of infiltrating macrophages. A tumor nodule is visible in the top left of the image with an inflammatory infiltrate surrounding it. Inset shows representative macrophages in the area outlined by the dashed box. (FIG. 10C). Immunohistochemical staining for F4/80, a mouse macrophage marker, in palpable subcutaneous tissue mass from a CV1-hIgG4 treated mouse. A tumor nodule is visible in the right portion of the image, with infiltrating macrophages stained on the left. Inset shows representative macrophages in the area outlined by the dashed box, with evidence of macrophages in the process of phagocytosis (black arrows) and successful engulfment of tumor cells (arrows). (FIG. 10D). Blood analysis of mice bearing GFP-luciferase+ 639-V bladder tumors on day 34 post-engraftment. CV1-hIgG4 treatment resulted in a moderate decrease in red blood cell indices. No toxicity to other blood lineages was observed.

FIG. 11A-11C. Treatment with high-affinity SIRPα monomers does not cause red blood cell toxicity. (FIG. 11A). Hematocrit measurements from mice over the course of treatment with the indicated therapies. (FIG. 11B). Hemoglobin levels from mice over the course of treatment with the indicated therapies. (FIG. 11C). Absolute red blood cell counts from mice over the course of treatment with the indicated therapies. (FIG. 11A-11C). ns=not significant. Black arrows indicate the start and stop of daily treatment.

FIG. 13A-13C. Radiolabelled high-affinity SIRPα variants are effective as non-invasive imaging agents for cancer. (FIG. 13A). NSG mice were subcutaneously engrafted with DLD-1 human colon cancer cells on the upper right flank. Tumor bearing mice were injected with Cu-64-labeled FD6 monomer and imaged by PET scan. Arrowheads indicate uptake by tumor, black arrowheads indicate uptake by kidneys. Upper panels show dorsal images, and lower panels show transverse sections through tumors. M2, M3 represent images from two independent animals. (FIG. 13B). Quantification of signal from animals over time. FD6 persists in the tumor for at least 24 hours. (FIG. 13C). Table showing presence of radiolabeled FD6 in tumor and normal tissues. T:N=ratio of uptake in tumor to indicated tissue. ID/g=injected dose per gram tissue.

FIG. 14A-14F. Fluorescence-activated cell sorting of macrophages demonstrates high-affinity SIRPα variants induce phagocytosis of cancer cells. (FIG. 14A) Primary human macrophages and GFP+ DLD-1 colon cancer cells were co-cultured in the presence of 100 nM CV1-hIgG4. Phagocytosis was quantified as the percentage of CD45+ macrophages that became GFP+. Macrophage populations were sorted by flow cytometry for those that were GFP negative, GFP low, or GFP high. (FIG. 14B) Sorted GFP-high macrophages contain engulfed tumor cells as visualized by microscopy under brightfield transmitted light (upper image) and fluorescent light (lower image; CD45, and GFP). (FIG. 14C) Wright-Giemsa staining of DLD-1 colon cancer cells. (FIG. 14D) Wright-Giemsa staining of sorted GFP-negative macrophage populations lacking engulfed material. (FIG. 14E) Wright-Giemsa staining of sorted GFP-low macrophage populations enriched for engulfed material. (FIG. 14F) Wright-Giemsa staining of sorted GFP-high macrophage populations containing engulfed tumor cells. B-F Scale bar represents 100 μm.

(FIG. 16A) Schematic showing high-affinity SIRPα variants. (FIG. 16B) Analytical gel filtration showing high-affinity SIRPα-Fc fusion proteins are purified as a single species (elution volume=13.44) with limited aggregation. (FIG. 16C) Phagocytosis assay with RFP+ mouse macrophages and GFP+ human lymphoma Raji cells. CD47 blockade with High-affinity SIRPα variant CV1 monomer or anti-CD47 Fab fragments produced marginal increases in phagocytosis, while treatment with high-affinity SIRPα-Fc or intact anti-CD47 antibodies produced elevated phagocytosis. (FIG. 16D) Oligomerization of CD47 does not induce phagocytosis. Phagocytosis assay performed with primary human macrophages and GFP+ DLD-1 human colon cancer cells. Treatment with high-affinity SIRPα dimers that lack a pro-phagocytic stimulus do not induce substantial levels of phagocytosis.

(FIG. 17A). Binding of high-affinity SIRPα variant FD6, but not wild-type allele 1 human SIRPα, to mouse CT26 colon cancer cells. (FIG. 17B). High-affinity SIRPα variant FD6-Fc blocks binding of wild-type mouse SIRPα tetramers to mouse CD47 displayed on the surface of yeast. (FIG. 17C). High-affinity SIRPα variant CV1 binds mouse CD47 displayed on the surface of yeast. (FIG. 17D). Binding of 100 nM wild-type allele 2 SIRPα-Fc, high-affinity SIRPα-Fc, or anti-CD47 antibodies (clones B6H12 and 5F9) to canine MDCK cells, as detected by flow cytometry with an anti-human IgG secondary antibody.

DEFINITIONS

Figure 2A:
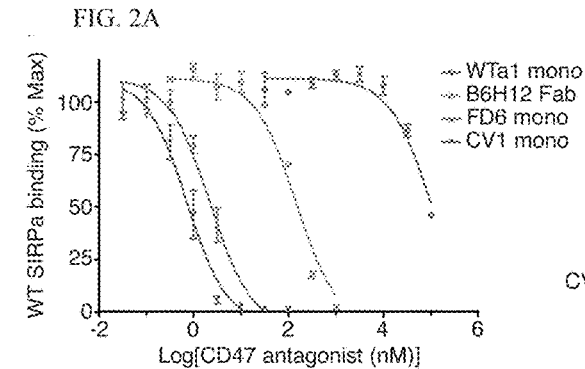
FIG. 2A-2H. High-affinity SIRPα variants block CD47 and stimulate phagocytosis in vitro.

In the description that follows, a number of terms conventionally used in the field of cell culture are utilized. In order to provide a clear and consistent understanding of the specification and claims, and the scope to be given to such terms, the following definitions are provided.

The terms "inhibitors," "blocking agents" and "masking agents" of the interaction between SIRPα and its ligand CD47 refer to molecules that prevent the binding of SIRPα and CD47. For development purposes the binding may be performed under experimental conditions, e.g. using isolated proteins as binding partners, using portions of proteins as binding partners, using yeast display of proteins or portions of proteins as binding partners, and the like.

For physiologically relevant purposes the binding of SIRPα and CD47 is usually an event between two cells, where each cell expresses one of the binding partners. Of particular interest is the expression of SIRPα on phagocytic cells, such as macrophages; and the expression of CD47 on cells that could be targets for phagocytosis, e.g. tumor cells, circulating hematopoietic cells, and the like. Inhibitors may be identified using in vitro and in vivo assays for receptor or ligand binding or signaling.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer. Subjects may be human, but also include other mammals, particularly those mammals useful as laboratory models for human disease, e.g. mouse, rat, etc.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration or prevention of an cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic and the compounds as used herein. When administered in combination, each component can be administered at the same time or sequentially in any order at different points in time. Thus, each component can be administered separately but sufficiently closely in time so as to provide the desired therapeutic effect.

In some embodiments, treatment is accomplished by administering a combination of a high affinity SIRPα reagent of the invention with a cytotoxic agent. One exemplary class of cytotoxic agents are chemotherapeutic agents. Exemplary chemotherapeutic agents include, but are not limited to, aldesleukin, altretamine, amifostine, asparaginase, bleomycin, capecitabine, carboplatin, carmustine, cladribine, cisapride, cisplatin, cyclophosphamide, cytarabine, dacarbazine (DTIC), dactinomycin, docetaxel, doxorubicin, dronabinol, duocarmycin, etoposide, filgrastim, fludarabine, fluorouracil, gemcitabine, granisetron, hydroxyurea, idarubicin, ifosfamide, interferon alpha, irinotecan, lansoprazole, levamisole, leucovorin, megestrol, mesna, methotrexate, metoclopramide, mitomycin, mitotane, mitoxantrone, omeprazole, ondansetron, paclitaxel (Taxol™), pilocarpine, prochloroperazine, rituximab, saproin, tamoxifen, taxol, topotecan hydrochloride, trastuzumab, vinblastine, vincristine and vinorelbine tartrate.

In other embodiments, administration of a high affinity SIRPα reagent of the invention is combined with an effective dose of an agent that increases patient hematocrit, for example erythropoietin stimulating agents (ESA). Such agents are known and used in the art, including, for example, Aranesp® (darbepoetin alfa), Epogen®NF/Procrit®NF (epoetin alfa), Omontys® (peginesatide), Procrit®, etc.

Other combination therapies include administration with cell-specific antibodies, for example antibodies selective for tumor cell markers, radiation, surgery, and/or hormone deprivation (Kwon et al., Proc. Natl. Acad. Sci U.S.A., 96:15074-9, 1999). Angiogenesis inhibitors can also be combined with the methods of the invention.

A number of antibodies are currently in clinical use for the treatment of cancer, and others are in varying stages of clinical development. For example, there are a number of antigens and corresponding monoclonal antibodies for the treatment of B cell malignancies. One target antigen is CD20. Rituximab is a chimeric unconjugated monoclonal antibody directed at the CD20 antigen. CD20 has an important functional role in B cell activation, proliferation, and differentiation. The CD52 antigen is targeted by the monoclonal antibody alemtuzumab, which is indicated for treatment of chronic lymphocytic leukemia. CD22 is targeted by a number of antibodies, and has recently demonstrated efficacy combined with toxin in chemotherapy-resistant hairy cell leukemia. Two new monoclonal antibodies targeting CD20, tositumomab and ibritumomab, have been submitted to the Food and Drug Administration (FDA). These antibodies are conjugated with radioisotopes. Alemtuzumab (Campath) is used in the treatment of chronic lymphocytic leukemia; Gemtuzumab (Mylotarg) finds use in the treatment of acute myelogenous leukemia; Ibritumomab (Zevalin) finds use in the treatment of non-Hodgkin's lymphoma; Panitumumab (Vectibix) finds use in the treatment of colon cancer. Monoclonal antibodies useful in the methods of the invention that have been used in solid tumors include, without limitation, edrecolomab and trastuzumab (herceptin). Edrecolomab targets the 17-1A antigen seen in colon and rectal cancer, and has been approved for use in Europe for these indications. Trastuzumab targets the HER-2/neu antigen. This antigen is seen on 25% to 35% of breast cancers. Cetuximab (Erbitux) is also of interest for use in the methods of the invention. The antibody binds to the EGF receptor (EGFR), and has been used in the treatment of solid tumors including colon cancer and squamous cell carcinoma of the head and neck (SCCHN).

In addition to cancer therapies, the SIRPα reagents of the invention are useful in other therapies in which monoclonal antibodies are administered for the purpose of depleting cells, e.g. in the treatment of inflammatory diseases by depletion immune cells. For such purposes the SIRPα reagent of the invention is administered in combination with a therapeutic antibody, e.g. with rituximab for depletion of B cells in inflammatory diseases and autoimmune conditions; alemtuzumab for multiple sclerosis; OKT3 for immunosuppression; others for bone marrow transplant conditioning; and the like.

"Concomitant administration" of a cancer therapeutic drug, ESA or tumor-directed antibody with a pharmaceutical composition of the present invention means administration with the high affinity SIRPα reagent at such time that both the drug, ESA or antibody and the composition of the present invention will have a therapeutic effect. Such concomitant administration may involve concurrent (i.e. at the same time), prior, or subsequent administration of the drug, ESA or antibody with respect to the administration of a compound of the invention. A person of ordinary skill in the art would have no difficulty determining the appropriate timing, sequence and dosages of administration for particular drugs and compositions of the present invention.

As used herein, the phrase "disease-free survival," refers to the lack of such tumor recurrence and/or spread and the fate of a patient after diagnosis, with respect to the effects of the cancer on the life-span of the patient. The phrase "overall survival" refers to the fate of the patient after diagnosis, despite the possibility that the cause of death in a patient is not directly due to the effects of the cancer. The phrases, "likelihood of disease-free survival", "risk of recurrence" and variants thereof, refer to the probability of tumor recurrence or spread in a patient subsequent to diagnosis of cancer, wherein the probability is determined according to the process of the invention.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., C16 alkyl esters. When there are two acidic groups present, a pharmaceutically acceptable salt or ester can be a monoacid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

DETAILED DESCRIPTION OF THE EMBODIMENTS

High affinity SIRPα polypeptides and analogs thereof are provided, which may be referred to generically as high affinity SIRPα reagents. The reagents are variants of the native human SIRPα protein. In one embodiment, the present invention provides a soluble SIRPα variant polypeptide, wherein the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

According to the present invention, amino acid changes include any naturally occurring or man-made amino acid modifications known or later discovered in the field. In some embodiments, amino acid changes include, e.g., substitution, deletion, addition, insertion, etc. of one or more amino acids. In some embodiments, amino acid changes include replacing an existing amino acid with another amino acid. In related embodiments, amino acid changes include replacing one or more existing amino acids with non-natural amino acids, or inserting one or more non-natural amino acids. Amino acid changes may be made in at least 1, 2, 3, 4, 5, 6, 7, 8, 9, 10, 11, 12 or more amino acid residues relative to a native sequence. The one or more amino acid changes alter properties of SIRPα, e.g., affecting the stability, binding activity and/or specificity, etc.

The high affinity SIRPα reagent of the invention comprises at least one amino acid modification within the d1 domain of SIRPα, which domain is set forth in SEQ ID NO:1, and corresponds to residues 31 to 149 of the native human full-length human protein. The high affinity SIRPα reagent can consist of all or a portion of the d1 domain; and may further comprise one or more amino acids from SIRPα outside of the d1 domain; or may comprise amino acid sequences other than SIRPα, which include without limitation immunoglobulin Fc region sequences.

High affinity SIRPα polypeptides can be at least about 100 amino acids in length, at least about 110, at least about 120, at least about 150, at least about 200 amino acids in length, up to the full-length of the wild-type protein at the transmembrane domain, i.e. about 343 amino acids in length, and is optionally fused to a heterologous polypeptide, e.g. immunoglobulin Fc.

In other embodiments, shorter peptides within the d1 domain and comprising at least one amino acid change set forth herein find use, where such peptides usually comprise a contiguous stretch of amino acids from a sequence set forth herein of not more than 10 amino acids in length, not more than 15 amino acids in length, not more than 20, not more than 25, not more than 30 amino acids, not more than 35 amino acids, not more than 40 amino acids, not more than 45 amino acids, not more than 50 amino acids, not more than 55 amino acids, not more than 60 amino acids, not more than 65 amino acids, not more than 70 amino acids, not more than 75 amino acids, not more than 80 amino acids, not more than 85 amino acids, not more than 90 amino acids, not more than 95 amino acids, not more than 100 amino acids.

In some embodiments, amino acid changes in the high affinity SIRPα polypeptide are made at one or more of the amino acids within the set of hydrophobic core residues of SIRPα, which include, without limitation, residues (numbering defined by the wild type sequence of the d1 domain, set forth as SEQ ID NO:1) L4, V6, V27, I36, F39, L48, I49, Y50, F57, V60, M72, F74, I76, V92, F94 and F103. In alternative embodiments the amino acid changes are made on the wild-type allele 2 sequence, e.g. as shown for CV1.

In other embodiments, amino acid changes are made at one or more of the amino acids within the set of contact residues that interact with CD47, which include, without limitation, A29, L30, I31, P32, V33, G34, P35, Q52, K53, E54, S66, T67, K68, R69, F74, K93, K96, G97, S98, and D100 (SEQ ID NO:1).

In other embodiments, amino acid changes are made at two or more, three or more, four or more, five or more, and not more than 14 amino acids within the combined set of contact residues and the set of hydrophobic core residues defined above.

In some embodiments, amino acid changes are made at one or more of the amino acids within the set that includes, without limitation, residues L4, V6, A21, V27, I31, E47, K53, E54, H56, S66, V63, K68, V92, F94, and F103, or a combination thereof, for example at two or more, three or more, four or more, five or more, six or more, seven or more, and not more than 15 residues.

In some embodiments the high affinity SIRPα reagent comprises at least one amino acid change selected from (1) L4V; L4I; (2) V6I; V6L; (3) A21V; (4) V27I; V27L; (5) I31T; I31S; I31F; (6) E47V; E47L; (7) K53R; (8) E54Q; (9) H56P; H56R; (10) S66T; S66G; (11) K68R; (12) V92I; (13) F94L; F94V; (14) V63I; and (15) F103V. In some embodiments the high affinity SIRPα polypeptide comprises modifications selected from (1) to (15) above, at two, three, four, five, six, seven, eight, nine, 10, 11, 12, 13, 14 or all 15 of the residues; and combinations and conservative equivalents thereof.

Sets of amino acid changes may include combinations of the above, for example:
V27I or V27L; K53R; S66T or S66G; K68R; and F103V.
L4V or L4I; V27I or V27L; E47V or E47L; K53R; E54Q; S66T or S66G; K68R; V92I; and F103V.
L4V or L4I; V6I or V6L; A21V; V27I or V27L; I31T, I31S or I31F; E47V or E47L; K53R; H56P or H56R; S66T or S66G; K68R; and F94L or F94V.
V6I or V6L; V27I or V27L; I31T, I31S, or I31F; E47V or E47L; K53R; E54Q; H56P or H56R; S66T or S66G; V92I; and F94L or F94V.

L4V or L4I; A21V; V27I or V27L; I31T, I31S, or I31F; E47V or E47L; K53R; E54Q; H56P or H56R; S66T or S66G; F94L or F94V; and F103V.

L4V or L4I; V6I or V6L; V27I or V27L; I31T, I31S, or I31F; E47V or E47L; K53R; H56P or H56R; S66T or S66G; K68R; V92I; and F94L or F94V.

L4V or L4I; V6I or V6L; I31T, I31S, or I31F; E47V, or E47L; K53R; H56P or H56R; S66T, or S66G; V92I; and F103V.

V6I; V27I; I31F; E47L; K53R; E54Q; H56P; and S66T.

L4V; V6I; V27I; I31F; E47V; K53R; E54Q; H56P; V63I; S66T; K68R; and V92I.

V6I; V27I; I31T; E47V; K53R; E54Q; H56P; S66G; K68R; V92I; and F103V.

V6I; V27I; I31F; E47V; K53R; E54Q; H56P; S66T; and V92I.

In some embodiments, the high affinity SIRPα polypeptide comprises the set of amino acid changes:

{V27I; K53R; S66T; S66G; K68R; F103V} for example as shown in (SEQ ID NO:3);

{L4V; V27L; E47V; K53R; E54Q; S66G; K68R; V92I} for example as shown in (SEQ ID NO: 4);

{L4V; V6I; A21V; V27I; I31T; E47L; K53R; H56P; S66T; K68R; F94L} for example as shown in (SEQ ID NO:5);

{V6I; V27I; I31S; I31F; E47V; K53R; E54Q; H56P; S66G; V92I; F94L} for example as shown in (SEQ ID NO:6);

{L4I; A21V; V27I; I31F; E47V; K53R; E54Q; H56R; S66G; F94V; F103V} for example as shown in (SEQ ID NO:7);

{L4V; V6I; V27I; I31F; E47V; K53R; H56R; S66G; K68R; V92I; F94L} for example as shown in (SEQ ID NO:8); or {L4V; V6L; I31F; E47V; K53R; H56P; S66G; V92I; F103V} for example as shown in (SEQ ID NO: 9)

{V6I; V27I; I31F; E47L; K53R; E54Q; H56P; S66T} for example as shown in SEQ ID NO: 37.

{L4V; V6I; V27I; I31F; E47V; K53R; E54Q; H56P; V63I; S66T; K68R; V92I} for example as shown in SEQ ID NO:38.

{V6I; V27I; I31T; E47V; K53R; E54Q; H56P; S66G; K68R; V92I; F103V} for example as shown in SEQ ID NO:39.

{V6I; V27I; I31F; E47V; K53R; E54Q; H56P; S66T; V92I} for example as shown in SEQ ID NO: 10.

For the purposes of the invention, a reagent of the invention comprises the portion of SIRPα that is sufficient to bind CD47 at a recognizable affinity, e.g., high affinity, which normally lies between the signal sequence and the transmembrane domain, or a fragment thereof that retains the binding activity. The high affinity SIRPα reagent will usually comprise at least the d1 domain of SIRPα (SEQ ID NO:1) with modified amino acid residues as described above. The high affinity SIRPα polypeptide may comprise at least amino acids 1-3, 7-20, 32-46, 69-91, 95-102 of a wild-type SIRPα d1 polypeptide (SEQ ID NO: 1) or an allelic variant thereof, i.e. wild-type allele 2. The high affinity SIRPα polypeptide may further comprise portions of the native human SIRPα protein other than the d1 domain, including without limitation residues 150 to 374 of the native protein (set forth as SEQ ID NO:2), or including, without limitation, at least 10 contiguous amino acids of the sequence set forth in SEQ ID NO:2, at least 20 contiguous amino acids, at least 50 contiguous amino acids, at least 100 contiguous amino acids, at least 125 contiguous amino acids, at least 250 contiguous amino acids or more.

High affinity SIRPα reagents of the present invention can be further modified, e.g., joined to a wide variety of other oligopeptides or proteins for a variety of purposes. For example, post-translationally modified, for example by pre-nylation, acetylation, amidation, carboxylation, glycosylation, pegylation, etc. Such modifications can also include modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. In some embodiments, SIRPα variants of the present invention include SIRPα variants having phosphorylated amino acid residues, e.g. phosphotyrosine, phosphoserine, or phosphothreonine.

In one embodiment, the high affinity SIRPα reagent has a kinetic $K_D$ of at least about $1\times10^{-8}$ M for CD47. In another embodiment, the high affinity SIRPα reagent has a kinetic $K_D$ of at least about $1\times10^{-9}$ M for CD47. In yet another embodiment, the high affinity SIRPα reagent has a kinetic $K_D$ of at least about $1\times10\ 10$ M for CD47. In various embodiments described herein, the high affinity SIRPα reagent exhibits a kinetic $K_D$ to CD47 that is at least about 5-fold greater than the kinetic $K_D$ of the native human SIRPα polypeptide, exemplified in SEQ ID NO:1 and 2. In some embodiments, the high affinity SIRPα reagent has a kinetic $K_D$ to CD47 that is at least about 10-fold, 50-fold, 100-fold, 500-fold, 1000-fold greater than the kinetic $K_D$ of the native SIRPα polypeptide.

Binding to CD47 can be determined, for example, by the ability of the SIRPα reagent to bind to CD47 coated on an assay plate; displayed on a microbial cell surface; in solution; etc. The binding activity of SIRPα variants of the present invention to CD47 can be assayed by immobilizing the ligand, e.g., CD47 or the SIRPα variant, to a bead, substrate, cell, etc. Agents can be added in an appropriate buffer and the binding partners incubated for a period of time at a given temperature. After washes to remove unbound material, the bound protein can be released with, for example, SDS, buffers with a high pH, and the like and analyzed.

In some embodiments, a SIRPα variant of the present invention is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. In other embodiments, the second polypeptide is any suitable polypeptide that is substantially similar to Fc, e.g., providing increased size, multimerization domains, and/or additional binding or interaction with Ig molecules. These fusion proteins can facilitate purification, multimerization, and show an increased half-life in vivo. Fusion proteins having disulfide-linked multimeric structures can also be more efficient in binding and neutralizing other molecules than a monomeric SIRPα.

In some embodiments the high affinity SIRPα binding domain, i.e. a SIRPα d1 domain modified as set forth herein to provide for high affinity binding to CD47, is provided as a multimeric protein, i.e. two, three, four or more SIRPα binding domains are covalently or non-covalently linked, e.g. as a fusion protein; disulfide bonded; through biotin binding to avidin, streptavidin, etc. Such multimeric high affinity SIRPα binding proteins are useful as single agents to increase phagocytosis of cells expressing CD47; or in combination with other binding agents, e.g. cell-specific monoclonal antibodies.

In some such embodiments, the high affinity SIRPα binding domain is fused or otherwise joined to an immunoglobulin sequence to form a chimeric protein. The immunoglobulin sequence preferably, but not necessarily, is immunoglobulin constant domain(s). The immunoglobulin moiety in such chimeras may be obtained from any species, usually human, and includes IgG1, IgG2, IgG3 or IgG4 subtypes, IgA, IgE, IgD or IgM. The immunoglobulin moiety may comprise one or more domains, e.g. CH1, CH2, CH3, etc.

Chimeras constructed from a sequence linked to an appropriate immunoglobulin constant domain sequence are known in the art. In such fusions the encoded chimeric polypeptide may retain at least functionally active hinge, CH2 and CH3 domains of the constant region of an immunoglobulin heavy chain. Fusions are also made to the C-terminus of the Fc portion of a constant domain, or immediately N-terminal to the CH1 of the heavy chain or the corresponding region of the light chain. The precise site at which the fusion is made is not critical; particular sites are well known and may be selected in order to optimize the biological activity, secretion or binding characteristics of the SIRPα polypeptide-immunoglobulin chimeras. In some embodiments, the SIRPα polypeptide-immunoglobulin chimeras are assembled as monomers, or hetero- or homo-multimers, and particularly as dimers or tetramers.

Although the presence of an immunoglobulin light chain is not required, an immunoglobulin light chain may be included, either covalently associated to an SIRPα polypeptide-immunoglobulin heavy chain fusion polypeptide, or directly fused to the SIRPα polypeptide. A single chain construct may be used to provide both heavy and light chain constant regions.

In other fusion protein constructs, the second polypeptide is a marker sequence, such as a peptide that facilitates purification of the fused polypeptide. For example, the marker amino acid sequence can be a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824, 1989, for instance, hexa-histidine provides for convenient purification of the fusion protein. Another peptide tag useful for purification, the "HA" tag, corresponds to an epitope derived from the influenza hemagglutinin protein. Wilson et al., Cell 37:767, 1984. The addition of peptide moieties to facilitate handling of polypeptides are familiar and routine techniques in the art.

In other embodiments the high affinity SIRPα binding domain is provided as a monomeric protein, which may be an isolated d1 domain, or a d1 domain fused to SIRPα or chimeric sequences. Monomeric SIRPα binding domains are useful, for example, as an adjuvant to increase the phagocytosis of cells expressing CD47, when combined with a cell-specific binding agent, e.g. an antibody, particularly a tumor cell specific antibody as defined herein. Monomeric SIRPα binding domains are also useful as adjuvants for increasing phagocytosis, as well as other immune functions, e.g. ADCC, uptake of antigens for antigen presentation, and the like by a number of immune cells, such as macrophages, dendritic cells, neutrophils, granulocytes and the like, which express SIRPα and respond to blockade with the SIRPα reagents of the invention. Monomeric high affinity SIRPα binding domains are also useful as imaging agents, e.g. when conjugated to a detectable label.

In some other embodiments, high affinity SIRPα reagents of the invention include reagents further modified to improve their resistance to proteolytic degradation or to optimize solubility properties or to render them more suitable as a therapeutic agent. For example, variants of the present invention further include analogs containing residues other than naturally occurring L-amino acids, e.g. D-amino acids or non-naturally occurring synthetic amino acids. D-amino acids may be substituted for some or all of the amino acid residues.

In some embodiments of the invention, the high affinity SIRPα reagent is coupled or conjugated to one or more imaging moieties, i.e. a detectable label. As used herein, "cytotoxic moiety" refers to a moiety that inhibits cell growth or promotes cell death when proximate to or absorbed by the cell. Suitable cytotoxic moieties in this regard include radioactive isotopes (radionuclides), chemotoxic agents such as differentiation inducers and small chemotoxic drugs, toxin proteins, and derivatives thereof.

As utilized herein, "imaging moiety", or detectable label, refers to a moiety that can be utilized to increase contrast between a tumor and the surrounding healthy tissue in a visualization technique, e.g., radiography, positron-emission tomography, magnetic resonance imaging, direct or indirect visual inspection. Thus, suitable imaging moieties include radiography moieties, e.g. heavy metals and radiation emitting moieties, positron emitting moieties, magnetic resonance contrast moieties, and optically visible moieties (e.g., fluorescent or visible-spectrum dyes, visible particles, etc. It will be appreciated by one of ordinary skill that some overlap exists between what is a therapeutic moiety and what is an imaging moiety.

In general, therapeutic or imaging agents can be conjugated to the high affinity SIRPα reagent moiety by any suitable technique, with appropriate consideration of the need for pharmacokinetic stability and reduced overall toxicity to the patient. A direct reaction between an agent and SIRPα is possible when each possesses a functional group capable of reacting with the other. For example, a nucleophilic group, such as an amino or sulfhydryl group, may be capable of reacting with a carbonyl-containing group, such as an anhydride or an acid halide, or with an alkyl group containing a good leaving group (e.g., a halide). Alternatively, a suitable chemical linker group may be used. A linker group can function as a spacer in order to avoid interference with binding capabilities.

It will be evident to those skilled in the art that a variety of bifunctional or polyfunctional reagents, both homo- and hetero-functional (such as those described in the catalog of the Pierce Chemical Co., Rockford, Ill.), may be employed as a linker group. Coupling may be effected, for example, through amino groups, carboxyl groups, sulfhydryl groups or oxidized carbohydrate residues. There are numerous references describing such methodology. Alternatively the SIRPα is linked to the cytotoxic or imaging moiety by the use of a non-covalent binding pair, such as streptavidin/biotin, or avidin/biotin. In these embodiments, one member of the pair is covalently coupled to SIRPα and the other member of the binding pair is covalently coupled to the cytotoxic or imaging moiety. It may be desirable to couple more than one cytotoxic and/or imaging moiety. By poly-derivatizing the high affinity SIRPα reagent, several strategies may be simultaneously implemented, an antibody may be made useful as a contrasting agent for several visualization techniques, or a therapeutic antibody may be labeled for tracking by a visualization technique.

A carrier may bear the agents in a variety of ways, including covalent bonding either directly or via a linker group, and non-covalent associations. Suitable covalent-bond carriers include proteins such as albumins, peptides, and polysaccharides such as aminodextran, each of which have multiple sites for the attachment of moieties. A carrier may also bear an agent by non-covalent associations, such as non-covalent bonding or by encapsulation Carriers and linkers specific for radionuclide agents include radiohalogenated small molecules and chelating compounds. A radionuclide chelate may be formed from chelating compounds that include those containing nitrogen and sulfur atoms as the donor atoms for binding the metal, or metal oxide, radionuclide.

Radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the compositions and methods of the invention. Such moieties may be conjugated to the high affinity SIRPα reagent antibody moiety through an acceptable chemical linker or chelation carrier. Positron emitting moieties for use in the present invention include $^{18}$F, which can be easily conjugated by a fluorination reaction with the high affinity SIRPα reagent.

Magnetic resonance contrast moieties include chelates of chromium (III), manganese (II), iron (II), nickel (II), copper (II), praseodymium (III), neodymium (III), samarium (III) and ytterbium (III) ion. Because of their very strong magnetic moment, the gadolinium (III), terbium (III), dysprosium (III), holmium (III), erbium (III), and iron (III) ions are especially preferred.

Optically visible moieties for use as imaging moieties include fluorescent dyes, or visible-spectrum dyes, visible particles, and other visible labeling moieties. Fluorescent dyes such as fluorescein, coumarin, rhodamine, bodipy Texas red, and cyanine dyes, are useful when sufficient excitation energy can be provided to the site to be inspected visually. Endoscopic visualization procedures may be more compatible with the use of such labels. Acceptable dyes include FDA-approved food dyes and colors, which are non-toxic, although pharmaceutically acceptable dyes which have been approved for internal administration are preferred.

The effective amount of an imaging conjugate compositions to be given to a particular patient will depend on a variety of factors, several of which will be different from patient to patient. A competent clinician will be able to determine an effective amount to facilitate the visualization of a tumor. Dosage will depend on the treatment of the tumor, route of administration, the nature of the therapeutics, sensitivity of the tumor to the therapeutics, etc. Utilizing ordinary skill, the competent clinician will be able to optimize the dosage of a particular therapeutic or imaging composition in the course of routine clinical trials.

A typical dose may be from 0.001 to 100 milligrams of conjugate per kilogram subject body weight. Relatively large doses, in the range of 0.1 to 10 mg per kilogram of patient body weight may be used for imaging conjugates with a relatively non-toxic imaging moiety. The amount utilized will depend on the sensitivity of the imaging method, and the relative toxicity of the imaging moiety.

SIRPα variants of the present invention can be produced by any suitable means known or later discovered in the field, e.g., produced from eukaryotic or prokaryotic cells, synthesized in vitro, etc. Where the protein is produced by prokaryotic cells, it may be further processed by unfolding, e.g. heat denaturation, DTT reduction, etc. and may be further refolded, using methods known in the art.

The polypeptides may be prepared by cell-free translation systems, or synthetic in vitro synthesis, using conventional methods as known in the art. Various commercial synthetic apparatuses are available, for example, automated synthesizers by Applied Biosystems, Inc., Foster City, CA, Beckman, etc. By using synthesizers, naturally occurring amino acids may be substituted with unnatural amino acids. The particular sequence and the manner of preparation will be determined by convenience, economics, purity required, and the like.

The polypeptides may also be isolated and purified in accordance with conventional methods of recombinant synthesis. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for therapeutic purposes, usually at least about 99.5% by weight, in relation to contaminants related to the method of preparation of the product and its purification. Usually, the percentages will be based upon total protein.

Methods which are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized. One of skill in the art can readily utilize well-known codon usage tables and synthetic methods to provide a suitable coding sequence for any of the polypeptides of the invention. The nucleic acids may be isolated and obtained in substantial purity. Usually, the nucleic acids, either as DNA or RNA, will be obtained substantially free of other naturally-occurring nucleic acid sequences, generally being at least about 50%, usually at least about 90% pure and are typically "recombinant," e.g., flanked by one or more nucleotides with which it is not normally associated on a naturally occurring chromosome. The nucleic acids of the invention can be provided as a linear molecule or within a circular molecule, and can be provided within autonomously replicating molecules (vectors) or within molecules without replication sequences. Expression of the nucleic acids can be regulated by their own or by other regulatory sequences known in the art. The nucleic acids of the invention can be introduced into suitable host cells using a variety of techniques available in the art.

According to the present invention, SIRPα variants can be provided in pharmaceutical compositions suitable for therapeutic use, e.g. for human treatment. In some embodiments, pharmaceutical compositions of the present invention include one or more therapeutic entities of the present invention or pharmaceutically acceptable salts, esters or solvates thereof. In some other embodiments, pharmaceutical compositions of the present invention include one or more therapeutic entities of the present invention in combination with another therapeutic agent, e.g., another anti-tumor agent.

Therapeutic entities of the present invention are often administered as pharmaceutical compositions comprising an active therapeutic agent and a other pharmaceutically acceptable excipient. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

In still some other embodiments, pharmaceutical compositions of the present invention can also include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

Methods of Use

Methods are provided for treating, reducing or preventing cancer, including without limitation lymphomas, leukemias, carcinomas, melanomas, glioblastomas, sarcomas, myelomas, etc. as primary or metastatic cancers, by inhibiting the interaction between SIRPα and CD47, thereby increasing in vivo phagocytosis of the tumor cells. Such methods include administering to a subject in need of treatment a therapeutically effective amount or an effective dose of a high affinity SIRPα reagent of the invention, including without limitation combinations of the reagent with a chemotherapeutic drug, a tumor-specific antibody, or an ESA.

Effective doses of the therapeutic entity of the present invention, e.g. for the treatment of cancer, vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In some embodiments, the therapeutic dosage may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still other embodiments, methods of the present invention include treating, reducing or preventing tumor growth, tumor metastasis or tumor invasion of cancers including lymphomas, leukemias, carcinomas, melanomas, glioblastomas, sarcomas, myelomas, etc. For prophylactic applications, pharmaceutical compositions or medicaments are administered to a patient susceptible to, or otherwise at risk of disease in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

The high affinity SIRPα polypeptides of the invention can be used in vitro and in vivo to monitor the course of disease therapy, for example, by measuring the increase or decrease in the number of cells expressing CD47, particularly cancer cells expressing CD47, it can be determined whether a particular therapeutic regimen aimed at ameliorating disease is effective. For such purposes, the SIRPα polypeptide may be detectably labeled.

The high affinity SIRPα polypeptides of the invention may be used in vitro in binding assays in which they can be utilized in liquid phase or bound to a solid phase carrier. In addition, the polypeptides in these immunoassays can be detectably labeled in various ways. Examples of types of assays which can utilize high affinity SIRPα polypeptides of the invention are flow cytometry, e.g. FACS, MACS, histochemistry, competitive and non-competitive immunoassays in either a direct or indirect format; and the like. Detection of CD47 using the high affinity SIRPα polypeptides can be done with assays which are run in either the forward, reverse, or simultaneous modes, including histochemical assays on physiological samples. Those of skill in the art will know, or can readily discern, other assay formats without undue experimentation.

The high affinity SIRPα polypeptides can be bound to many different carriers and used to detect the presence of CD47 expressing cells. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding proteins, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the polypeptides of the invention, or will be able to ascertain such, using routine experimentation. Furthermore, the binding of these labels to the polypeptides of the invention can be done using standard techniques common to those of ordinary skill in the art.

CD47 may be detected by the high affinity SIRPα polypeptides of the invention when present in biological fluids and tissues. Any sample containing a detectable amount of CD47 can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

Another labeling technique which may result in greater sensitivity consists of coupling the polypeptides to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

The imaging conjugates of a high affinity SIRPα reagent can be administered to the subject in a series of more than one administration. The imaging conjugate compositions may be administered at an appropriate time before the visualization technique. For example, administration within an hour before direct visual inspection may be appropriate, or administration within twelve hours before an MRI scan may be appropriate. Care should be taken, however, to not allow too much time to pass between administration and visualization, as the imaging compound may eventually be cleared from the patient's system.

Compositions for the treatment of cancer can be administered by parenteral, topical, intravenous, intratumoral, oral, subcutaneous, intraarterial, intracranial, intraperitoneal, intranasal or intramuscular means. A typical route of administration is intravenous or intratumoral, although other routes can be equally effective.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249:1527, 1990 and Hanes, Advanced Drug Delivery Reviews 28:97-119, 1997. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the high affinity SIRPα reagents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

Also within the scope of the invention are kits comprising the compositions (e.g., high affinity SIRPα reagents and formulations thereof) of the invention and instructions for use. The kit can further contain a least one additional reagent, e.g. a chemotherapeutic drug, anti-tumor antibody, ESA, etc. Kits typically include a label indicating the intended use of the contents of the kit. The term label includes any writing, or recorded material supplied on or with the kit, or which otherwise accompanies the kit.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Protein expression and purification: The IgSF domain of human CD47 (residues 19-135) and variants of the first IgSF domain of human SIRPα (residues 31-148) were cloned into pAcGP67 with C-terminal 8×Histidine tags and expressed in Hi5 cells using recombinant baculovirus. The free cysteine on the CD47 IgSF domain was mutated to glycine. Proteins were purified by Ni-NTA chromatography and gel filtration over a Superdex-75 column into HBS (10 mM Hepes pH 7.4, 150 mM NaCl). To produce biotinylated proteins, a C-terminal biotin acceptor peptide (BAP)-LNDIFEAQK-IEWHE (SEQ ID NO:46) tag was added and proteins were co-expressed with BirA ligase with excess biotin (100 µM). For crystallization, SIRPα variant FD6 was expressed in the E. coli periplasm with an N-terminal maltose-binding protein (MBP) tag, which was removed by treatment with 3C protease. The CD47 IgSF domain was co-expressed with EndoF in Hi5 cells in the presence of kifunensine to remove glycosylation.

For expression of SIRPα variant proteins as fusions to human IgG4 and IgG2 Fc chains, SIRPα variants were cloned into pFUSE-hIgG4-Fc2 and pFUSE-hIgG2-Fc2 vectors (Invivogen) in frame with the IL2 signal sequence. SIRPα variant fusion proteins were expressed in Freestyle 293-F cells (Invitrogen) following transfection with 293fectin (Invitrogen). Supernatants were harvested after 96 hours of protein expression and purified over HiTrap Protein A columns (GE Healthcare).

Crystallization and structural determination of FD6:CD47 complex: E. coli derived FD6 and deglycosylated, insect-derived CD47 were mixed at a 1:1 ratio and treated with carboxypeptidase A and B, followed by gel filtration over a Superdex-75 column into HBS. The complex was concentrated to 22 mg/mL and crystallized by vapor diffusion in sitting drops by addition of 0.1 µL of protein to an equal volume of 2.0M Ammonium Sulfate, 0.1M Tris pH 7.3. Diffraction studies were performed at the Advanced Light Source. Crystal structures were solved by molecular replacement with PHASER and refined using PHENIX and COOT.

Surface Plasmon Resonance: SPR experiments were conducted on a Biacore T100 instrument at 25° C. Experiments used a Biacore SA sensor chip (GE Healthcare) to capture biotinylated CD47 at a surface density of approximately 150 RU. An unrelated biotinylated protein was immobilized as a reference surface for the SA sensor chip with matching RU to the experimental surface. Serial dilutions of unbiotinylated SIRPα variants in the running buffer [1×HBS-P (GE Healthcare)] were flowed over the chip at a rate of 50 µL/min. CD47 was regenerated using three 30 second injections of 2M $MgCl_2$. Data was analyzed using the Biacore T100 evaluation software version 2.0 with a 1:1 Langmuir binding model.

Cancer cell lines and culture conditions: Jurkat cells (ATCC) and DLD-1 cells (ATCC) were maintained in RPMI (Invitrogen)+10% fetal bovine serum (Omega Scientific)+1% GlutaMax (Invitrogen)+1% penicillin/streptomycin solution (Invitrogen). Jurkat cells were maintained in suspension, while DLD-1 cells were maintained as adherent monolayers. Both cell lines were passage in regular intervals of 3-4 days before reaching confluency. To make GFP-luciferase+ cell lines, Jurkat and DLD-1 cells were transduced with a luciferase2 (Promega)-eGFP expressing lentivirus derived from the pCDH-CMV-MCS-EF1-puro HIV-based lentiviral vector (Systems Bioscience). Cells were sorted for GFP+ cells using a BD FACSAria II flow cytometer and maintained in culture in the same manner as the parental lines.

Evaluation of SIRPα variant binding to human cancer cells: GFP+ Jurkat cells were washed in PBS then incubated with titrating concentrations of biotinylated SIRPα variants for 30 minutes on ice. Wild-type SIRPα tetramer was pre-formed by incubating a 4:1 molar ratio of biotinylated wild-type SIRPα with streptavidin for 15 minutes on ice. Cells were washed in FACS buffer (PBS+2% FBS), then incubated with 50 nM streptavidin conjugated to Alexa Fluor 647 for 20 minutes on ice. Cells were washed twice then analyzed for SIRPα variant binding by flow cytometry using an Accuri C6 flow cytometer. To assess blocking of wild-type SIRPα to cD47, 50M wild-type SIRPα tetramer was incubated with titrating concentrations of CD47 blocking agents for 30 minutes on ice. Anti-CD47 clone B6H12 (eBioscience) was used as a positive control for blocking. Data were analyzed using GraphPad Prism 5. Maximal SIRPα variant binding represents the percentage of the maximal mean fluorescence intensity measured for each variant.

Macrophage derivation and culture: For derivation of human macrophages, leukocyte reduction system chambers were obtained from the Stanford Blood Center from anonymous donors. Peripheral blood mononuclear cells were obtained by centrifugation over a Ficoll Paque Premium (GE Healthcare) density gradient. CD14+ monocytes were purified using CD14 microbeads (Miltenyi) and an AutoMACS Pro Separator (Miltenyi). Monocytes were differentiated to macrophages by culturing in IMDM+GlutaMax (Invitrogen)+10% AB human serum (Invitrogen)+1% penicillin/ streptomycin for 7 days at which time they were used for phagocytosis assays.

Mouse macrophages were derived by isolating bone marrow from C57Bl/Ka Rosa26-mRFP1 transgenic mice and culturing in RPMI (Invitrogen)+10% FBS+1% GlutaMax+ 1% penicillin/streptomycin supplemented with 10 µg/mL murine M-CSF (Peprotech). After 7 days of differentiation, macrophages were harvested and used for phagocytosis assays.

In vitro phagocytosis assays: In vitro phagocytosis assays were performed using mouse and human macrophages. For evaluation by flow cytometry, approximately 50,000 macrophages were added per well in 96-well tissue culture plates. 200,000 GFP+ tumor cells were pre-incubated for 30 minutes with antibody or SIRPα variant therapies in serum-free medium then added to the macrophages. Anti-CD47 clone 2D3 (eBioscience) and cetuximab (Bristol-Myers Squibb) were used as described for opsonization. Macrophages and target cells were incubated for 2 hours in a humidified 37° incubator containing 5% carbon dioxide. Following the incubation, cells were washed, removed from the plate, and prepared for flow cytometry. Dead cells were excluded from the analysis by staining with DAPI (Invitrogen). Human macrophages were identified by staining with Alexa Fluor 647 conjugated anti-human CD14 (BioLegend). Samples were analyzed using a BD Biosciences LSR-Fortessa with a high throughput sampler. The percentage of macrophages phagocytosing tumor cells, represented by GFP+ macrophages, was determined using FlowJo 7.6.4 (Treestar).

For visualization of phagocytosis in vitro, 50,000 macrophages were plated in 24-well plates. Tumor cells were labeled with 5 µM CFSE (Invitrogen) according to the manufacturer's protocol. 200,000 CFSE+ tumor cells were treated with antibody or SIRPα variant treatments for 30 minutes in serum-free medium, added to the macrophages, and then incubated at 37° for 2 hours. Following the incubation, wells were washed extensively to remove residual target cells. Subsequently, the wells were visualized using an inverted fluorescence microscope (Leica DMI6000 B). The phagocytosis index was scored as the number of target cells per macrophage multiplied by 100.

Results. In vivo experiments treating xenografted immunodeficient mice show that treatment with the high-affinity SIRPα-Fc reagents blocked tumor growth. Mice transplanted with luciferase expressing HL60 leukemia cells were treated with soluble SIRP reagents. Tumor burden as measured by radiance emitted from the luciferase-HL60 cells declined to background levels indicating clearance of the tumor cells, whereas the IgG control treated mice, the radiance increased, reflecting increased tumor growth. This result was comparable to that observed with the hu5F9 anti-CD47ab. These data show that the high affinity soluble SIRPα reagents are comparable to anti-CD47 antibody in effectively blocking the "don't eat me signal" by binding to the CD47 on the HL60 cell and allowing phagocytosis and clearance of the cells.

Example 2

High-Affinity SIRPα Lowers the Threshold for Macrophage Phagocytosis of Cancer Cells The ability of tumors to evade the immune system is an emerging hallmark of cancer, and new therapeutic strategies that direct immune responses against cancer cells show promise in experimental and clinical settings. Macrophages commonly infiltrate tumors, and recent studies have identified CD47 as an anti-phagocytic "don't eat me" signal that is highly expressed on many types of cancer to avoid macrophage-mediated destruction. Antibodies that block binding of CD47 to SIRPα, an inhibitory receptor on macrophages, greatly increase phagocytosis of cancer cells-identifying an exciting new axis to manipulate with anti-tumor immunotherapies. Directed evolution and protein engineering were used to modify the binding domain of SIRPα, whose wild-type affinity is too weak to be therapeutically useful, as a high-affinity competitive antagonist of CD47.

We created SIRPα variants that bind to CD47 with an approximately 50,000-fold increase in affinity relative to wild-type SIRPα. When produced as multimeric high affinity SIRPα-Fc fusion proteins, the variants act as single agents to induce phagocytosis in vitro and reduce growth of human tumors in vivo. While single domain high-affinity SIRPα monomers are not sufficient to induce maximal phagocytosis on their own, they greatly enhance the efficacy of established therapeutic monoclonal antibodies when given in combination therapies. Since CD47 is a pervasive mechanism that tumor cells use to evade the immune system, the molecules generated in this study benefit a large number of cancer patients, both as monotherapies and as adjuvants to other targeted biologics.

Figures 5A, 5B:
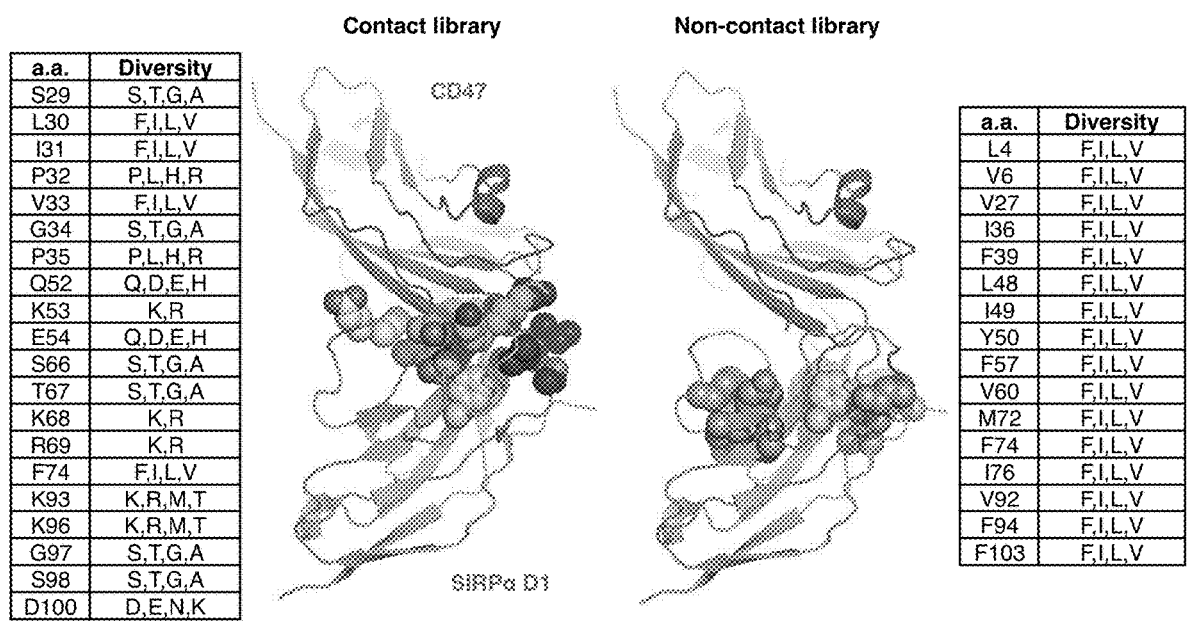
FIG. 5A-5B. Library design and sequences from first generation selections.
Figure 6:
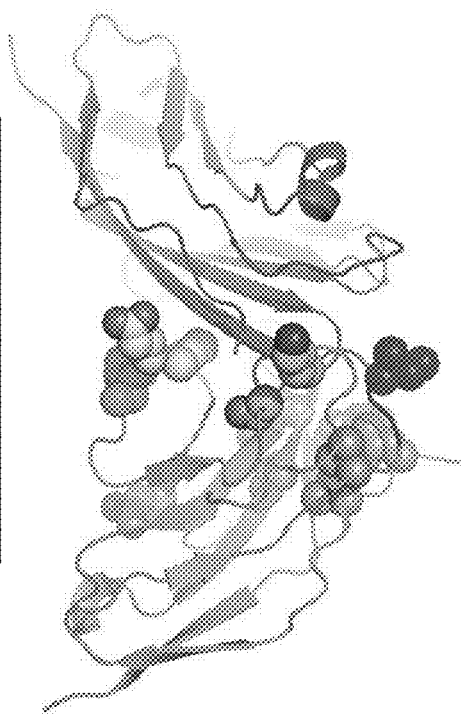
FIG. 6. Library design of second generation selections. Table of randomized positions and possible amino acids for the second generation library and the position of the variable residues within the structure of SIRPα. SIRPα is depicted, and CD47 is depicted, and the randomized positions are represented as space filling side chains.
Figure 7:
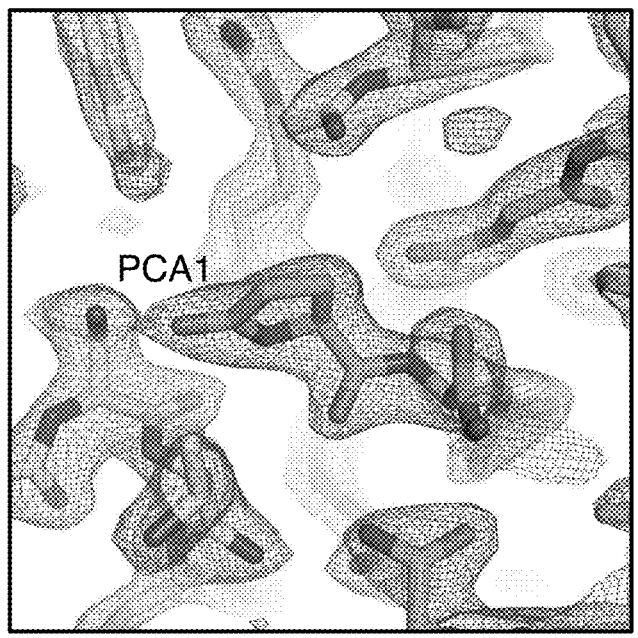
FIG. 7. Representative electron density map of FD6: CD47 complex. $2mF_o-DF_c$ electron density map contoured at $2.0\sigma$. Modeled amino acid residues are depicted as sticks, with FD6 residues and CD47 residues. Pyroglutamic acid residue 1 of CD47 is indicated as PCA1 above the corresponding residue and density.

To generate an ideal CD47 antagonist, protein engineering was used to improve the affinity of soluble SIRPα for CD47 (FIG. 1A). We created mutant libraries of the N-terminal V-set Ig domain of SIRPα conjugated to Aga2p for yeast surface-display (FIG. 1B). Using the CD47 IgSF domain as a selection reagent, we conducted two 'generations' of in vitro evolution. The first generation entailed five rounds of selection from a pooled mutant library containing randomizations to two classes of SIRPα residues-those that contact CD47 or those that reside within the hydrophobic core (FIG. 5A). The resulting first generation SIRPα variants bound CD47 with 20-100-fold higher affinity than wild type SIRPα, as measured by surface plasmon resonance. To obtain even higher-affinity variants, we performed a second generation of directed evolution by constructing a library that achieved full-coverage of thirteen residues mutated in the first generation selectants. After five additional rounds of selection, we obtained variants that bound CD47 with dissociation constants ($K_D$) as low as 34.0 pM and decay half-lives ($t_{1/2}$) as long as 44 minutes compared to 0.3-0.5 µM $K_D$ and 1.8 seconds $t_{1/2}$ for wild-type SIRPα (FIG. 1C). Interestingly, the sequences of the high-affinity SIRPα variants converged on a consensus set of mutations. When we grafted these nine conservative substitutions onto the predominant wild-type SIRPα allele (allele 2), the resulting variant (termed CV1, consensus variant 1) bound CD47 with an affinity of 11.1 pM (FIG. 1C).

The CV1 sequence has the following amino acid changes, relative to the wild-type allele: V6I; V27I; I31F; E47V; K53R; E54Q; H56P; S66T; V92I. CV1 may comprise, for example, a d1 domain amino acid sequence as follows:
(SEQ ID NO: 10) EEELQIIQPD KSVLVAAGET ATLRCTITSL FPVGPIQWER GAGPGRVLIY NQRQGPFPRV TTVSDTTKRN NMDESIRIGN ITPADAGTYY CIKFRKGSPD DVEEKSGAGT ELSVRAKPS To understand whether the high-affinity SIRPα variants retained a CD47-binding geometry similar to the wild-type protein, we determined the crystal structure of a complex between the high-affinity variant FD6 and the CD47 IgSF domain (FIG. 1D). The FD6:CD47 complex superimposed with the wild-type SIRPα:CD47 complex with a root mean square deviation of only 0.613 Å, indicating a high degree of structural similarity and validating our efforts to preserve the geometry of the wild type interaction (FIG. 1E). The overlapping binding modes of FD6 and wild-type SIRPα for CD47 indicate they would compete for the same CD47 epitope, thereby providing maximal potential antagonism. As a notable difference, the C'D loop of FD6 contains three of the four contact mutations present in the consensus sequence (FIG. 1E). We speculate these mutations stabilize the C'D loop, which positions the positive charge of Arg53 into a cluster of glutamic acids on CD47 (FIG. 1E). The remainder of the binding interface between FD6 and CD47 highly resembles the wild-type SIRPα:CD47 interface, with the most notable exception being the mutation of Ile31 to Phe. These structural studies indicate the high-affinity SIRPα variants can serve as efficacious CD47 antagonists.

Figure 8A:
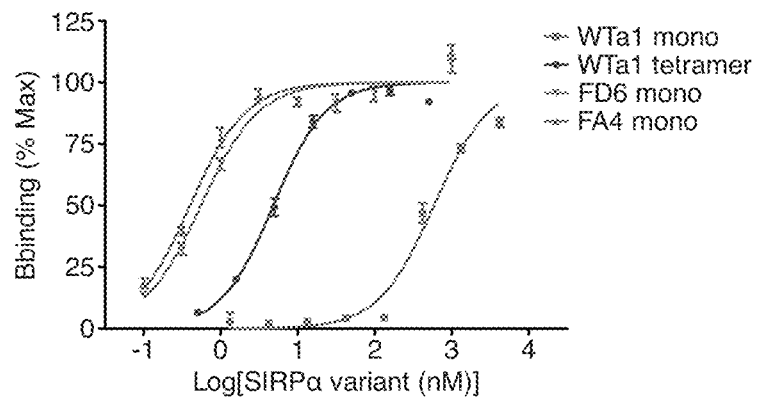
FIG. 8A-8C. High-affinity SIRPα variants potently bind and block CD47 on cancer cells.
Figure 8B:
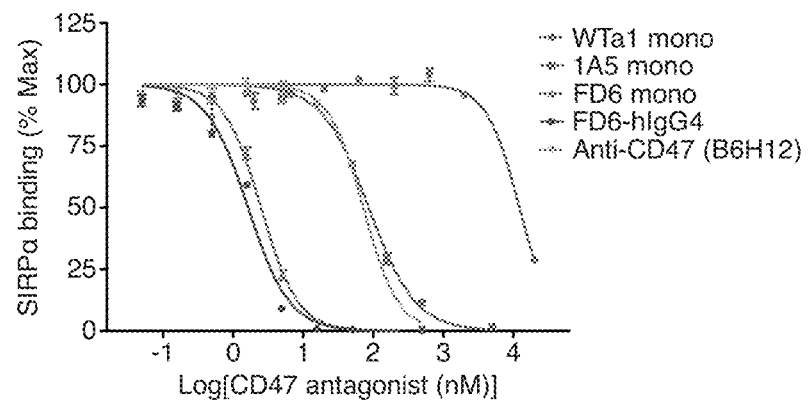
Figure 8C:
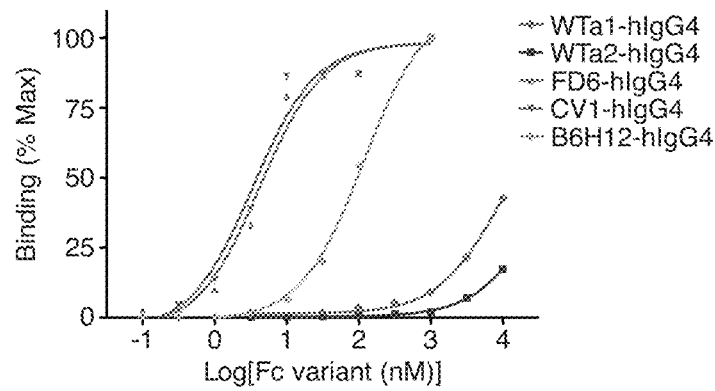

To test the functional properties of the high-affinity SIRPα variants, we first examined their ability to bind and antagonize CD47 on the surface of cancer cells. We found that SIRPα variants with increased CD47 affinity exhibited greater potency in binding (FIGS. 8a, c) and blocking cell-surface CD47 (FIG. 2a and FIG. 8b). As single domain monomers, both FD6 and CV1 variants exhibited potent antagonism relative to wild-type SIRPα. Importantly, both high-affinity variants were more potent CD47 antagonists than Fab fragments produced from anti-CD47 antibody clone B6H12, a well-characterized CD47 antagonist that demonstrates therapeutic efficacy in vitro and in vivo (FIG. 8a).

Figure 2B:
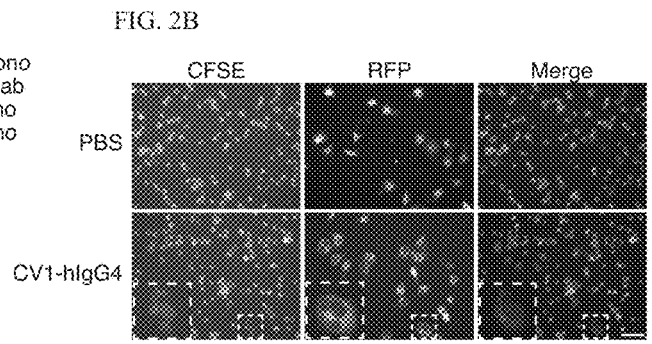
Figures 2C, 2D:
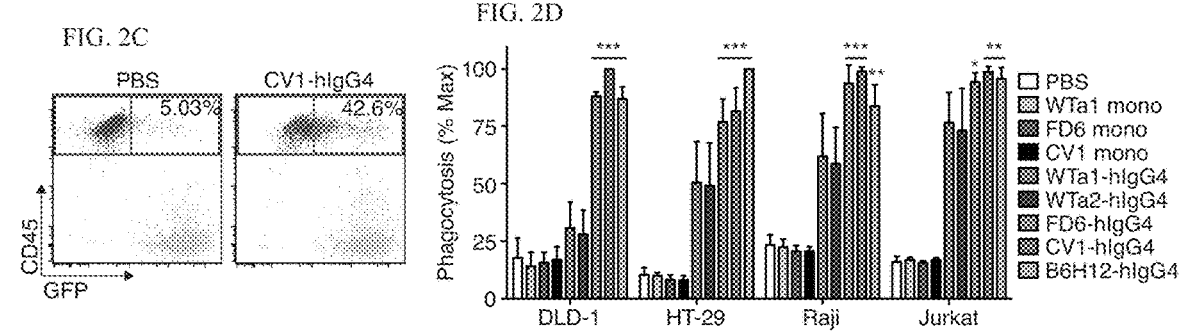
Figure 2E:
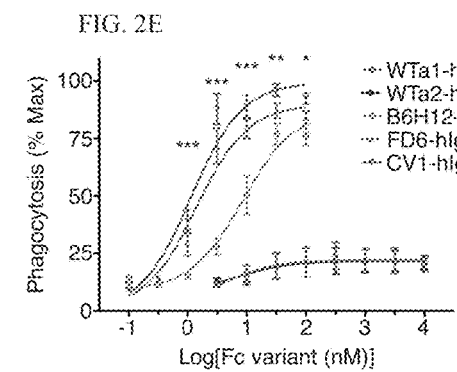

We next evaluated the ability of high-affinity SIRPα variants to increase phagocytosis in vitro by co-culturing macrophages and tumor cells in the presence of CD47 blocking agents. As fusion proteins to the Fc fragment of human IgG4 (hIgG4), the high-affinity SIRPα variants led to dramatic increases in phagocytosis of cancer cells as visualized by microscopy (FIG. 2b). To obtain quantitative measurements of phagocytosis, primary human macrophages and GFP+ tumor cells were co-cultured with CD47-blocking agents and then analyzed by flow cytometry (FIG. 2c). Using multiple cancer cell lines representing both solid and hematologic malignancies, we found that treatment with saturating concentrations of high-affinity SIRPα-hIgG4 variants produced dramatic increases in phagocytosis relative to wild-type SIRPα-hIgG4 controls (FIG. 2d). Although the high-affinity SIRPα-hIgG4 variants and an isotype-matched anti-CD47 antibody produced comparable levels of phagocytosis at saturating concentrations (FIG. 2d), the high-affinity SIRPα variants demonstrated a clear advantage when titrated to generate dose-response curves (FIG. 2e). The high affinities of FD6-hIgG4 and CV1-hIgG4 corresponded to decreased $EC_{50}$'s, indicating more potent induction of phagocytosis.

Figure 2F:
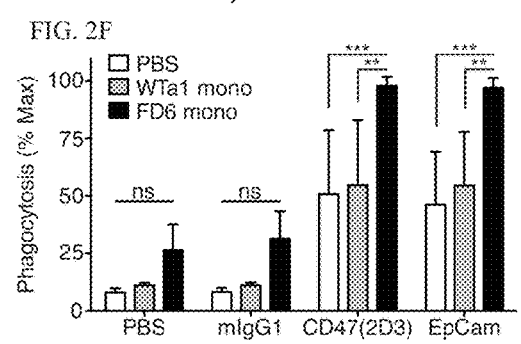

Interestingly, no substantial increases in phagocytosis were observed upon treatment with saturating concentrations of high-affinity SIRPα monomers (FIG. 2d), suggesting that blocking CD47 alone is not sufficient to induce maximal phagocytosis. Consequently, we hypothesized that treatment with high-affinity SIRPα monomers would lower the threshold for phagocytosis in the presence of tumor-specific monoclonal antibodies. To investigate this hypothesis, we performed phagocytosis assays using antibodies targeting DLD-1 cells, a human colon cancer cell line. When high-affinity SIRPα monomers were added alone or in combination with a nonspecific isotype control antibody, basal levels of phagocytosis were observed (FIG. 2f).

Treatment with either anti-CD47 clone 2D3, which binds CD47 but does not block the interaction with SIRPα, or an anti-EpCam antibody produced moderate levels of phagocytosis. However, upon addition of high-affinity SIRPα monomer FD6 to both antibody treatments, macrophages exhibited significant increases in phagocytosis (FIG. 2f). Thus, blocking CD47 lowers the threshold for macrophage phagocytosis in the presence of other activating stimuli, such as antibody Fc.

Figure 2G:
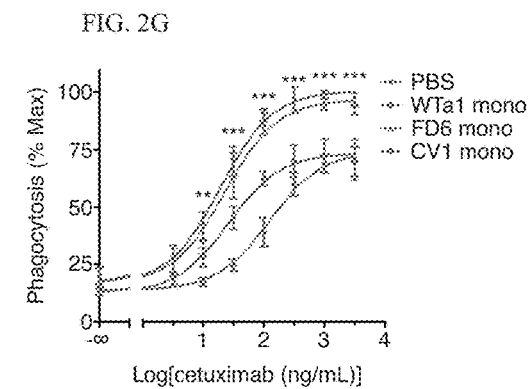
Figure 2H:
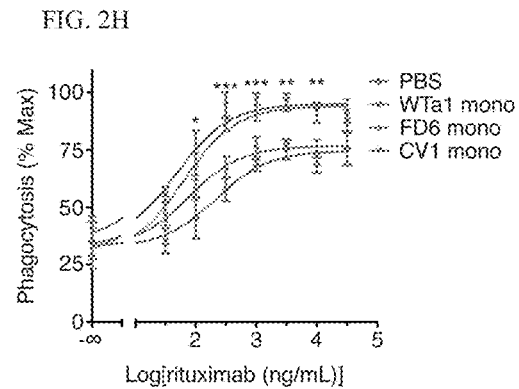

To demonstrate the clinical implications of this principle, we investigated the ability of high-affinity SIRPα monomers to enhance the efficacy of established monoclonal antibodies currently used as cancer therapies. First, phagocytosis assays were performed using DLD-1 colon cancer cells treated with the anti-EGFR antibody cetuximab. Phagocytosis was evaluated in response to titrating concentrations of cetuximab alone, in combination with wild-type SIRPα monomer, or in combination with high-affinity SIRPα monomers. Relative to both cetuximab alone or in combination with wild-type SIRPα monomer, the combination of cetuximab plus high-affinity SIRPα monomer produced a significant increase in both the maximal efficacy and potency of cetuximab (FIG. 2g). Similar effects were observed when phagocytosis was evaluated with Raji lymphoma cells treated with titrating concentrations of rituximab, an anti-CD20 antibody (FIG. 2h). Again, high-affinity SIRPα monomers increased both the maximal efficacy and potency of rituximab. In clinical settings, monoclonal antibodies often only achieve limited responses, and relapse is common following treatment. The high-affinity SIRPα monomers offer a solution to these problems by serving as universal adjuvants to tumor-specific antibodies.

Figure 3A:
FIG. 3A-3H. High-affinity SIRPα-Fc fusion proteins are effective as single agents for cancer.
Figure 3B:
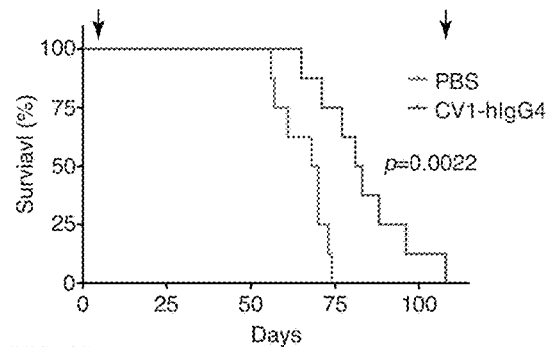
Figure 3C:
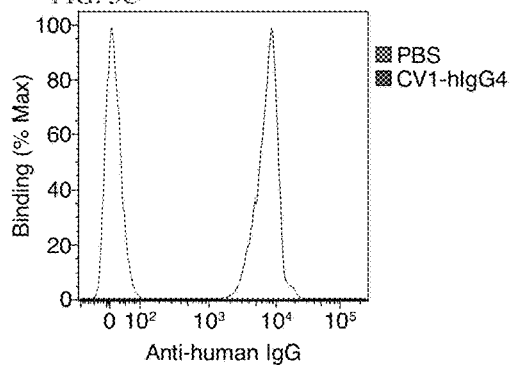
Figure 3D:
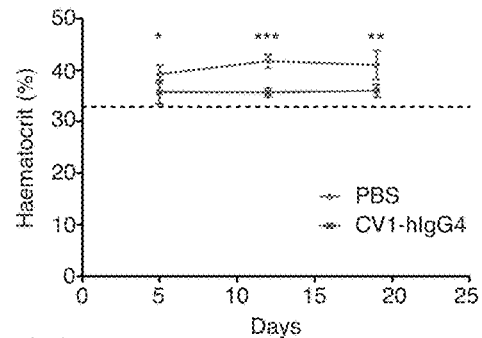
Figure 9:
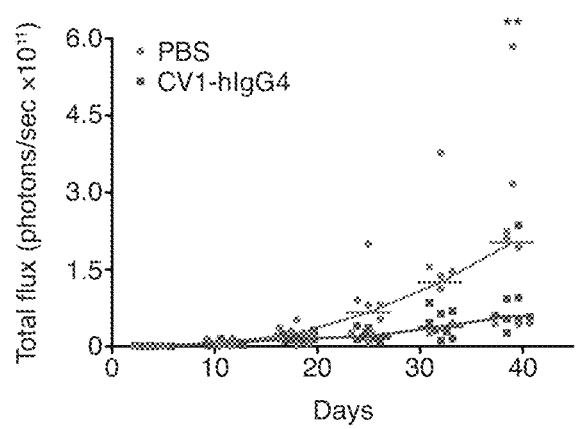
FIG. 9. High-affinity SIRPα-Fc variants restrict growth of DLD-1 colon cancer cells in vivo. Tumor growth curves upon treatment with vehicle (PBS) or high affinity SIRPα-hIgG4 fusion protein (CV1-hIgG4), as measured by bioluminescence imaging of the peritoneal cavities of treated mice. Points indicate values from individual mice, lines depict median values. $**p<0.01$ by 2-way ANOVA with Bonferroni post-test.
Figure 12:
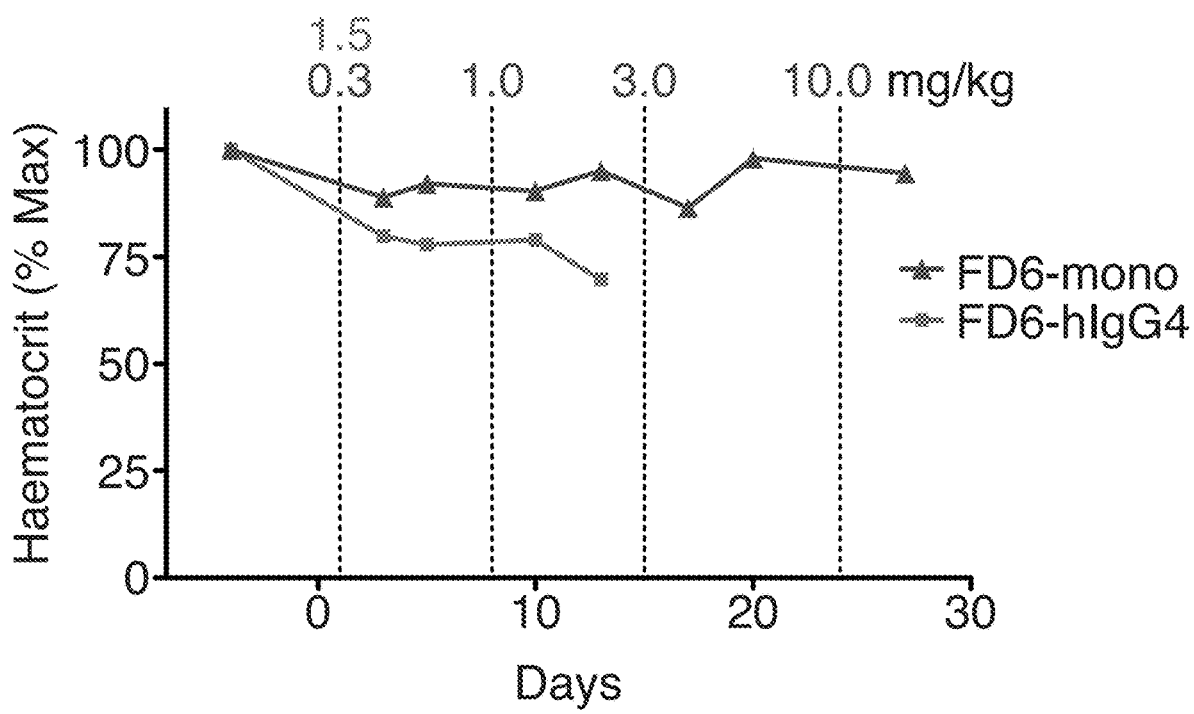
FIG. 12. High-affinity SIRPα variants exhibit safety in non-human primates. Cynomolgus monkeys were treated with a single intravenous injection of high-affinity SIRPα-Fc (FD6-hIgG4) or a dose-escalation series of high-affinity SIRPα monomer (FD6 mono). Dotted lines depict days of treatment with doses indicated above in mg/kg. Moderate toxicity to red blood cells was observed as a drop in hematocrit upon treatment with FD6-hIgG4, and no loss of red blood cells was observed with FD6 monomer therapy. No toxicity to other organ systems was observed.
Figure 15:
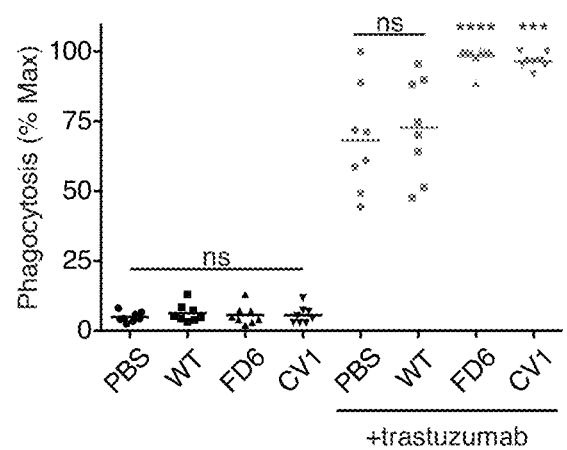
FIG. 15. High-affinity SIRPα variants synergize with trastuzumab for Her2+ breast cancer. Primary human macrophages were co-cultured with GFP+ SK-BR-3 breast cancer cells and the indicated therapies. Phagocytosis was evaluated by flow cytometry. The addition of high-affinity SIRPα monomer FD6 or CV1 to trastuzumab augmented phagocytosis. ns=not significant, *p<0.001, **p<0.0001 versus control treatments or wild-type SIRPα treatments in combination with trastuzumab.
Figure 16A:
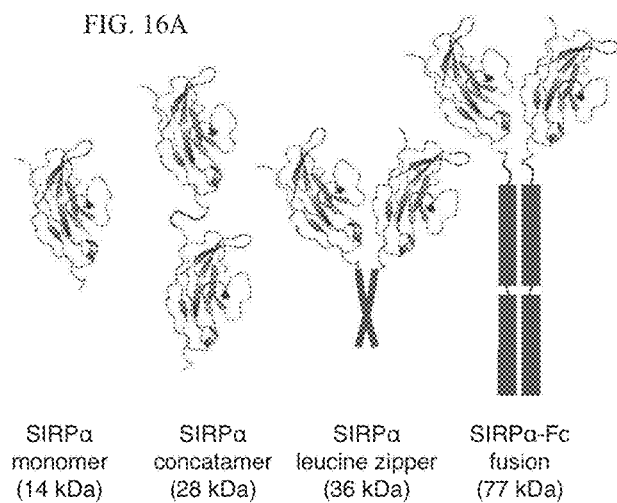
FIG. 16A-16D. High-affinity SIRPα variants induce maximal efficacy in the presence of tumor-bound antibody Fc chains.
Figure 16B:
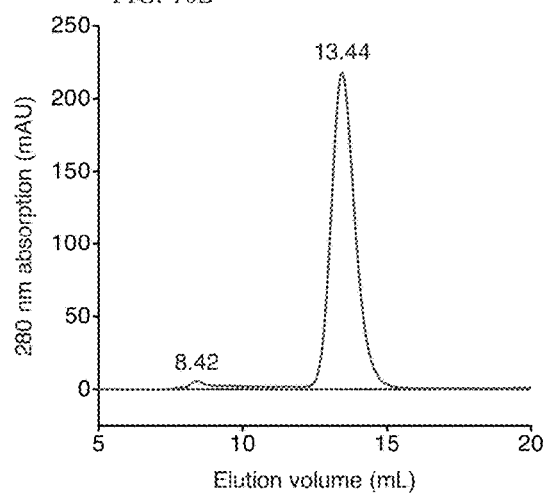
Figure 16C:
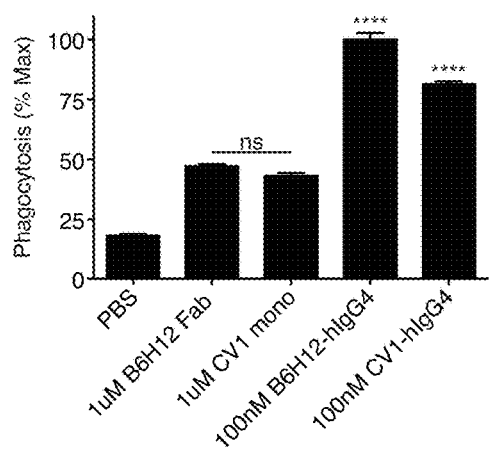
Figure 16D:
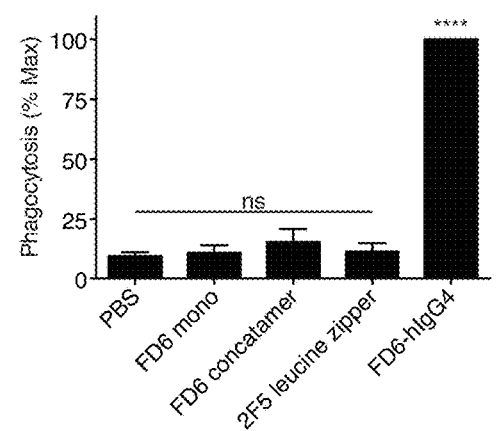
Figure 17A:
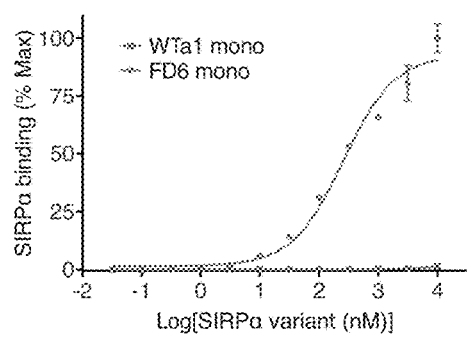
FIG. 17A-17D. High-affinity SIRPα variants bind and block other mammalian CD47 orthologs.
Figure 17B:
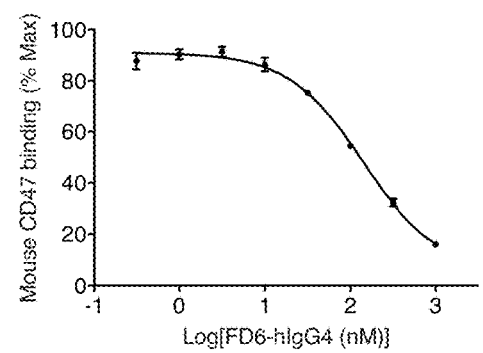
Figure 17C:
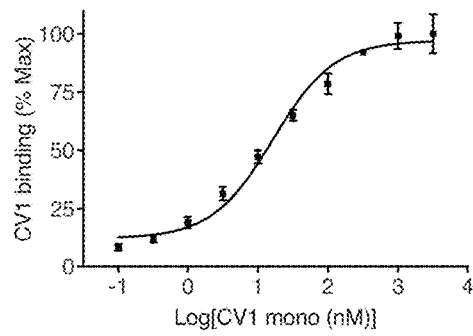
Figure 17D:
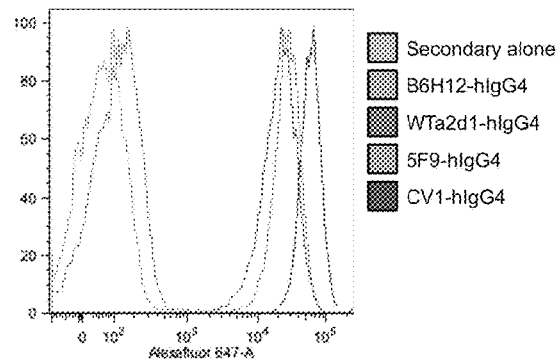

We next evaluated the efficacy of the high-affinity SIRPα variants in vivo using mouse tumor models. As an aggressive model of advanced stage human colon cancer, GFP-luciferase+ DLD-1 cells were engrafted into the peritoneal cavities of NSG mice (FIG. 3a). After confirming engraftment by bioluminescence imaging, daily treatment was initiated with vehicle control or high-affinity SIRPα variant CV1-hIgG4 as a monotherapy. Bioluminescence monitoring of total flux revealed a moderate decrease in tumor growth rates during the initial weeks of treatment with CV1-hIgG4 (FIG. 9), which led to a significant survival benefit over time (FIG. 3b). Since red blood cell loss is the major side effect observed upon treatment with anti-mouse CD47 antibodies, we examined the blood of CV1-hIgG4 treated mice for similar decreases. Flow cytometry revealed that CV1-hIgG4 bound all cells in the blood (FIG. 3c) and resulted in a moderate decrease in hematocrit (FIG. 3d). However, as previously observed, prolonged treatment did not cause further toxicity.

Figure 3E:
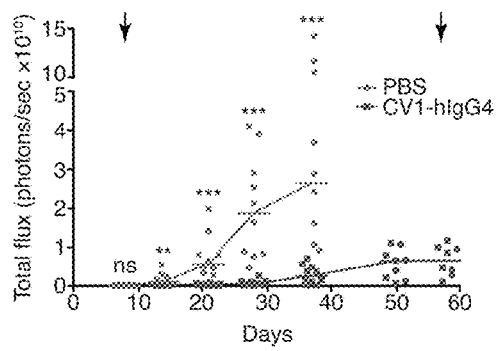
Figure 3F:
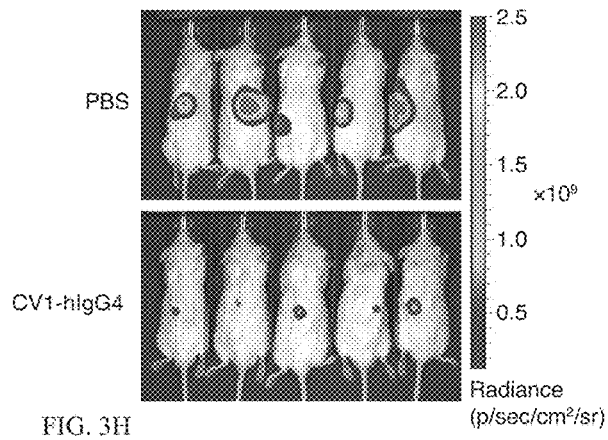
Figure 3G:
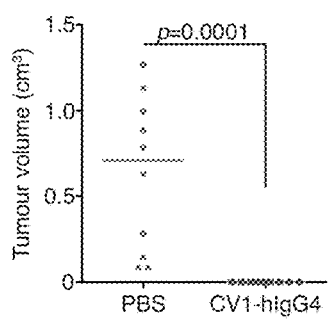
Figure 3H:
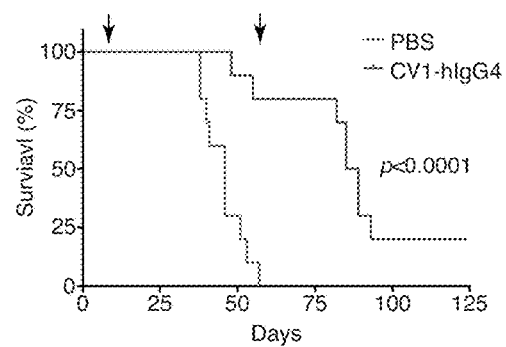

Since CV1-hIgG4 exhibited anti-tumor efficacy as a single agent, we next evaluated its efficacy in a model of human bladder cancer, a type of cancer for which no targeted biologics currently exist. GFP-luciferase+ 639-V bladder cancer cells were injected into the dorsal subcutaneous tissue of NSG mice. Engraftment was confirmed by bioluminescence imaging, and mice were randomized into groups for daily treatment with vehicle control or CV1-hIgG4. Treatment with CV1-hIgG4 substantially reduced tumor growth rates as evaluated by bioluminescence imaging (FIGS. 3e, f). Tumor volumes were assessed immediately prior to the death of the first control treated mouse, at which point large tumors were measureable in all control mice and no discernible tumors were palpable in the CV1-hIgG4 treated mice (FIG. 3g). Accordingly, a remarkable benefit in survival was observed, even after discontinuing treatment once all control mice had died (FIG. 3h).

As previously observed, treatment with CV1-hIgG4 resulted in decreases in red blood cell indices (FIG. 10a). CV1-hIgG4 treated mice also developed palpable stromal tissue surrounding the sites of tumor engraftment. Histopathological examination of this tissue revealed small tumor nodules embedded in an extensive inflammatory infiltrate containing macrophages (FIGS. 10b, c).

We next investigated the adjuvant effect of the high-affinity SIRPα monomers in vivo. In a localized model of human lymphoma, GFP-luciferase+ Raji cells were subcutaneously engrafted into the flanks of NSG mice. After confirming engraftment by bioluminescence imaging, mice were randomized into groups for a three-week course of daily treatment with either vehicle, CV1 monomer alone, rituximab alone, or a combination of rituximab plus CV1 monomer. Treatment with CV1 monomer or rituximab alone only reduced tumor growth, while treatment with the combination therapy dramatically eradicated tumors in the majority of mice (FIGS. 4a, b, c). During the treatment period, no significant red blood cell decreases were observed (FIGS. 11a, b, c). The effects of each therapy translated to respective trends in survival curves (FIG. 4d). Remarkably, the synergistic effect of combining a high affinity SIRPα monomer with a tumor-specific monoclonal antibody led to long-lasting cures in the majority of animals—even after treatment was discontinued (FIG. 4d).

The development of the high-affinity SIRPα variants represents a multidisciplinary, rational drug design effort, proceeding from molecular engineering at the protein level, to in vitro validation using purified immune effector cells, and finally to therapeutic evaluation in animal models. While previous studies have demonstrated the value of targeting the CD47-SIRPα interaction as an immune intervention for cancer, here we have further manipulated this system to generate highly efficacious and potent CD47 antagonists that exhibit optimal properties as therapeutics.

Our in vitro and in vivo findings provide new insight into the activity of macrophages against cancer and their response to immunomodulating therapies. As observed with high affinity SIRPα monomers, blockade of CD47 alone is not sufficient to induce maximal phagocytosis. Similarly, when CD47 is free to transduce inhibitory signals through SIRPα on macrophages, monoclonal antibodies do not achieve their maximal efficacy. However, macrophages are robustly stimulated when CD47 is blocked by high-affinity SIRPα monomers in the presence of surface-bound antibody Fc. High-affinity SIRPα-Fc fusion proteins and anti-CD47 antibodies combine a CD47 blocking component and a pro-phagocytic antibody Fc into a single molecule; hence they exhibit efficacy as single agents but have greater potential for off target toxicity. On the other hand, the combination of high-affinity SIRPα monomers with a separate anti-tumor monoclonal antibody, such as rituximab, specifically enhances anti-tumor responses. While this strategy offers clear benefits, particularly a lack of discernible toxicity, it is dependent on the availability and efficacy of clinically-approved monoclonal antibodies to achieve maximal responses.

A recent report suggested that wild-type SIRPα-Fc fusion proteins could be used to treat human leukemia. However, our study shows the weak affinity between wild-type SIRPα and CD47 limits the potential of such a therapy. The effects observed by others were likely mediated primarily by the pro-phagocytic effects of Fc, as opposed to CD47 antagonism, since phagocytosis was only apparent when macrophages were pre-activated with endotoxin and interferon-γ. In vivo, the lack of cross-reactivity between wild-type human SIRPα and mouse CD47 insufficiently models treatment and toxicity in humans where a large 'antigen sink' exists due to CD47 expression on all cells of the body.

The high-affinity SIRPα reagents constitute a novel class of anti-tumor biologics that are amenable to further engineering. Modifications can be designed to alter efficacy, specificity, tissue penetrance, clearance, and toxicity. Furthermore, since many tumors overexpress CD47 and expression levels correlate with poor patient outcomes, high-affinity SIRPα variants can be adapted as non-invasive imaging agents for cancer. CD47 is commonly used by tumor cells to evade the immune system, thus high-affinity SIRPα variants could be valuable therapeutics for a variety of human cancers. High-affinity SIRPα-Fc fusion proteins demonstrate efficacy as single agents, and thus can be particularly useful as treatments for cancers for which no targeted therapies currently exist. Moreover, high-affinity SIRPα monomers can be used as universal adjuvants to conventional monoclonal antibody therapies. Overall, this study deepens our knowledge of macrophage responses to malignant cells and supports use of the high-affinity SIRPα reagents as immune-based therapies for cancer.

Methods

Protein expression and purification. The CD47 IgSF domain (residues 1-117), with a C15G mutation and C-terminal 8. histidine tag, was secreted from *Trichoplusia ni* (Hi-5) cells using baculovirus and purified by Ni-NTA and size exclusion chromatography with a Superdex-75 column. To generate glycan-minimized CD47 for crystallography, CD47 was co-expressed with endoglycosidase-H (endoH) in the presence of kifunensine. Monomeric SIRPα variants (residues 1-118) were expressed as MBP-fusions in the periplasm of BL-21 (DE3) *E. coli* using a modified pMal-p2X expression vector (New England Biolabs) containing a rhinovirus 3C protease cleavage site after the MBP tag and a C-terminal 8·histidine tag. Cells were induced at an $OD_{600}$ of 0.8 with 1 mM IPTG and incubated with shaking at 22° C. for 24 hours. Periplasmic protein was obtained by osmotic shock and the MBP-fusion proteins were purified using nickel-nitrilotriacetic acid (Ni-NTA) chromatography. Eluted proteins were digested with 3C protease at 4° C. for 12 hours to remove MBP and further purified by an additional Ni-NTA chromatography step, followed by size exclusion chromatography with a Superdex-S75 column. For in vitro phagocytosis assays and in vivo experiments, endotoxin was removed using Triton X-114 as previously described and endotoxin removal confirmed using the ToxinSensor Chromogenic LAL Endotoxin Assay Kit (Genscript). SIRPα-Fc fusions were produced by cloning SIRPα variants into a modified pFUSE-hIgG4-Fc vector (Invivogen) with an IL-2 signal sequence and engineered Ser228 Pro mutation. Proteins were expressed by transient transfection in Freestyle 293-F cells (Invitrogen) and purified over HiTrap Protein A columns (GE Healthcare). Chimeric anti-CD47 clone B6H12-hIgG4 was recombinantly produced by stable expression in CHO cells (Lonza).

To obtain biotinylated CD47 and SIRPα, proteins were expressed with a carboxy terminal biotin acceptor peptide tag (GLNDIFEAQKIEWHE, SEQ ID NO 48) and purified as described above. The purified proteins were biotinylated in vitro with BirA ligase and then repurified from the reaction mixture by size exclusion chromatography.

Preparation of Fab fragments of B6H12. B6H12 antibody was desalted into 20 mM sodium citrate pH 6.0, 25 mM cysteine, 5 mM EDTA and diluted to a concentration of 4 mg/mL. The antibody was then mixed with 250 µL immobilized ficin resin (Thermo Scientific) per mL of antibody and incubated with rotation at 37° C. for five hours. The digested fragments were purified by passing the reaction mixture over a monoQ column (B6H12 Fab resided in the flow through), followed by gel filtration with a Superdex-200 column.

Yeast display and library generation of SIRPα variants. The N-terminal V-set domain of SIRPα (residues 1-118) was displayed on the surface of *S. cerevisiae* strain EBY100 as a C terminal fusion to Aga2 using the pCT302 vector as previously described. The pooled first generation library was generated by two separate assembly PCR reactions that randomized the CD47-contact residues and the hydrophobic 'core' residues of SIRPα, respectively, using the following primer sets with degenerate codons: Contact residue PCR primer set, randomizing Ser29=RST, Leu30=NTT, Ile31=NTT, Pro32=CNT, Val33=NTT, Gly34=RST, Pro35=CNT, Gln52=SAW, Lys53-ARG, Glu54=SAW, Ser66=RST, Thr67=RST, Lys68=ARG, Arg69=ARG, Phe74=NTT, Lys93=ANG, Lys96=ANG, Gly97=RST, Ser98=RST, and Asp100=RAS:

```
                                         (SEQ ID NO: 11)
5'GAGGAGGAGCTGCAGGTGATTCAGCCTGACAAGTCCGTATCAGTTGCA

GCT3';

(SEQ ID NO: 12)
5'GGTCACAGTGCAGTGCAGAATGGCCGACTCTCCAGCTGCAACTGATAC

GGA3';

(SEQ ID NO: 13)
5'CTGCACTGCACTGTGACCRSTNTTNTTCNTNTTRSTCNTATCCAGTGG

TTCAGAGGA3';

(SEQ ID NO: 14)
5'ATTGTAGATTAATTCCCGGGCTGGTCCAGCTCCTCTGAACCACTGGAT

3';

(SEQ ID NO: 15)
5'CGGGAATTAATCTACAATSAWARGSAWGGCCACTTCCCCCGGGTAACA

ACTGTTTCAGAG3';

(SEQ ID NO: 16)
5'GTTACTGATGCTGATGGAAANGTCCATGTTTTCCYTCYTASYASYCTC

TGAAACAGTTGTTAC3';

(SEQ ID NO: 17)
5'TCCATCAGCATCAGTAACATCACCCCAGCAGATGCCGGCACCTACTAC

TGTGTG3';

(SEQ ID NO: 18)
5'TCCAGACTTAAACTCCGTWTYAGGASYASYCNTCCGGAACNTCACACA

GTAGTAGGTGCC3';

(SEQ ID NO: 19)
5'ACGGAGTTTAAGTCTGGAGCAGGCACTGAGCTGTCTGTGCGTGCCAAA

CCCTCT3'
```

'Core' residue PCR primers, randomizing Leu4, Val6, Val27, Ile36, Phe38, Leu47, Ile49, Tyr50, Phe57, Val60, Met72, Phe74, Ile76, V92, Phe94, and Phe103 to NTT:

(SEQ ID NO: 20)
5'GGATCCGAGGAGGAGNTTCAGNTTATTCAGCCTGACAAGTCCGTATCA GTTGCAGCTGGAGAG3';

(SEQ ID NO: 21)
5'GGGCCCCACAGGGATCAGGGAGGTAANAGTGCAGTGCAGAATGGCCGA CTCTCCAGCTGCAAC3';

(SEQ ID NO: 22)
5'CTGATCCCTGTGGGGCCCNTTCAGTGGNTTAGAGGAGCTGGACCAGCC CGGGAA3';

(SEQ ID NO: 23)
5'GTGGCCTTCTTTTTGATTAANAANAANTTCCCGGGCTGGTCCAGC3';

(SEQ ID NO: 24)
5'AATCAAAAAGAAGGCCACNTTCCCCGGNTTACAACTGTTTCAGAGTCC ACAAAGAGAAAAC3';

(SEQ ID NO: 25)
5'GCCGGCATCTGCTGGGGTGATGTTACTGATGCTAANGGAAANGTCAAN GTTTTCTCTCTTTGTGGA3';

(SEQ ID NO: 26)
5'ACCCCAGCAGATGCCGGCACCTACTACTGTNTTAAGNTTCGGAAAGGG AGCCCTGACACGGAG3', (SEQ ID NO: 27)
5'AGAGGGTTTGGCACGCACAGACAGCTCAGTGCCTGCTCCAGACTTAAN CTCCGTGTCAGGGCTCCC3'.

The PCR products were further amplified with primers containing homology to the pCT302 vector, combined with linearized pCT302 vector DNA, and co-electroporated into EBY100 yeast. The resulting library contained 4.0·10⁸ transformants.

The second generation library was generated and transformed identically as the first generation library, but was assembled with the following primers, randomizing Leu4=NTT, Val6=NTT, Val27=NTT, Ile31=WYT, Glu47=SWA, Lys53-ARG, Glu54=SAK, His56=CNT, Ser66=RST, Lys68-ARG, Val92=NTT, Phe94=NTT, Phe103=NTT:

(SEQ ID NO: 28)
5'GGATCCGAGGAGGAGNTTCAGNTTATTCAGCCTGACAAGTCCGTAT C3';

(SEQ ID NO: 29)
5'GTGCAGTGCAGAATGGCCGACTCTCCAGCTGCAACTGATACGGACT TGTCAGGCTGAA3';

(SEQ ID NO: 30)
5'CATTCTGCACTGCACTNTTACCTCCCTGWYTCCTGTGGGCCCATC CAG3';

(SEQ ID NO: 31)
5'CGGGCTGGTCCAGCTCCTCTGAACCACTGGATGGGCCCCACAGG3';

(SEQ ID NO: 32)
5'GAGCTGGACCAGCCCGGSWATTAATCTACAATCAAARGSAKGGCCNT TCCCCCGGGTAACAACTGTTTCAGAG3;

(SEQ ID NO:33)
5'GAAAAGTCCATGTTTTCTCTCYTTGTASYCTCTGAAACAGTTGTTA C3';

(SEQ ID NO: 34)
5'AGAGAAAACATGGACTTTTCCATCAGCATCAGTAACATCACCCCAGC AGATGCC GGCAC3';

(SEQ ID NO: 35)
5'CTCCGTGTCAGGGCTCCCTTTCCGAANCTTAANACAGTAGTAGGTGC CGGCATC TGCTG3', (SEQ ID NO: 36)
5'GAGCCCTGACACGGAGNTTAAGTCTGGAGCAGGCACTGAGCTGTCTGT GCGTGCCAAACCCTCT3'.

The resulting library contained 2 x 108 transformants.

The resulting library contained 2×10⁸ transformants.

Selection of first generation library. Transformed yeast were expanded in SDCAA liquid media at 30° C. and induced in SGCAA liquid medium at 20° C. All selection steps were carried out at 4° C. For the first round of selection, 4×10⁹ induced yeast, representing ten-fold coverage of the number of library transformants, were resuspended in 5 mL PBE (phosphate buffered saline supplemented with 0.5% bovine serum albumin and 0.5 mM EDTA). Yeast were mixed with 500 µL paramagnetic streptavidin microbeads (Miltenyi) that were pre-coated with biotinylated CD47 and the mixture was incubated with rotation for one hour. The yeast were pelleted by centrifugation at 5,000 g for five minutes and washed twice with 10 mL PBE. Magnetically-labeled yeast were resuspended in 5 mL PBE and separated with an LS MACS column according to the manufacturer's instructions (Miltenyi). Eluted yeast were pelleted, resuspended in SDCAA medium, and expanded for the next round of selection. Four additional rounds of selection were performed similarly to the first round with the following modifications: 1×–10⁸ yeast were resuspended in 500 µl pbe containing fitc-labeled anti-c-myc antibody (Miltenyi) or successively decreasing concentrations of biotinylated CD47 protein, from 1 µM to 100 nM. After incubation for one hour, yeast were washed with PBE and for selections with CD47, labeled with streptavidin-PE (Invitrogen) or streptavidin-Alexa Fluor 647 (produced in house) for 15 minutes. Yeast were washed twice more with PBE and magnetically labeled with 50 µL of the appropriate anti-fluorophore microbeads (anti-FITC, anti-PE, or anti-Alexa Fluor 647; Miltenyi) for 15 minutes. Yeast were washed once, resuspended in 3 mL PBE, and separated with an LS column as in the first round.

Selection of second generation library. For the first two rounds of selection of the second generation library, yeast were selected with monomeric, biotinylated CD47 protein, as in rounds two through five of the first generation selections. The first round was selected with 20 nM biotinylated CD47 and the second round with 1 nM biotinylated CD47, using a larger staining volume (10 mL PBE) to avoid ligand depletion. For all subsequent rounds of selection, kinetic selection was performed. Briefly, yeast were stained with 20 nM biotinylated CD47 for one hour, washed with PBE, and then resuspended in 500 µL PBE containing 1 µM non-biotinylated CD47. The cells were incubated at 25° C. for 90 minutes (round three) or 300 minutes (rounds four and five), after which they were washed with ice-cold PBE and stained with fluorescently labeled streptavidin. For rounds one through four, yeast were separated using MACS, as described for the first generation library. For the fifth round of selection, yeast were co-labeled with FITC-labeled anti-c-Myc and streptavidin-Alexa Fluor 647 and selected with a FACSAria cell sorter (BD Biosciences).

Surface plasmon resonance (SPR). Experiments were conducted with a Biacore T100 at 25° C. Protein concentrations were quantified by 280 nm absorbance with a Nanodrop2000 spectrometer (Thermo Scientific). A Biacore SA sensor chip (GE Healthcare) was used to capture biotinylated CD47 ($R_{max}$ ~150 RU). An unrelated biotinylated protein was immobilized with an RU value matching that of the reference surface to control for nonspecific binding. Measurements were made with serial dilutions of the SIRPα variants in HBS-P+ buffer (GE Healthcare). The CD47 surface was regenerated by three 60 second injections of 2 M $MgCl_2$. All data were analyzed with the Biacore T100 evaluation software version 2.0 with a 1:1 Langmuir binding model.

Crystallization and structural determination of FD6:CD47 complex. Glycan-minimized CD47 and E. coli-derived FD6 were mixed at a 1:1 ratio and digested with carboxypeptidases A and B to remove their C-terminal 8× histidine tags. The digested FD6:CD47 complex was purified by gel filtration into HEPES buffered saline (HBS; 10 mM HEPES pH 7.4, 150 mM NaCl) with a Superdex-75 column and concentrated to 22 mg/mL. Crystals were obtained by addition of 0.1 µL protein to an equal volume of 2.0 M ammonium sulfate and 0.1 M Tris pH 7.3, and were cryoprotected in paraffin oil. Diffraction studies were performed at beamline 8-2 at the Advanced Light Source (Berkeley, CA, USA). An anisotropic 1.9 Å dataset was obtained and processed with HKL-3000. The FD6:CD47 complex was solved by molecular replacement with the individual models of CD47 and SIRPα from Protein Data Bank accession code 2JJS. Refinement was carried out using PHENIX and model adjustment performed with COOT. Bulk solvent flattening was used for solvent correction. Initial refinement used rigid body, coordinate, and real-space refinement, along with individual atomic displacement parameter refinement. TLS refinement was added in later refinement iterations.

Cell lines and GFP-luciferase+ transduction. DLD-1 cells (ATCC), HT-29 cells (ATCC), Raji cells (ATCC), Jurkat cells (ATCC), and 639-V cells (DSMZ) were cultured in RPMI+GlutaMax (Invitrogen) supplemented with 10% fetal bovine serum (Omega Scientific), 100 U/mL penicillin and 100 µg/mL streptomycin (Invitrogen). GFP-luciferase+ lines were generated by transduction using a pCDH-CMV-MCS-EF1 puro HIV-based lentiviral vector (Systems Biosciences) engineered to express an eGFP-luciferase2 (pg14) fusion protein. Stable lines were created by sorting for GFP expression on FACSAria II cell sorters (BD Biosciences).

Cell-based CD47 binding assays. Varying concentrations of biotinylated SIRPα monomers, SIRPα-hIgG4 fusion proteins, or anti-CD47 antibodies were incubated with cancer cells as indicated. Binding of biotinylated monomers was detected using 100 nM Alexa Fluor 647-conjugated streptavidin as a secondary staining reagent and was analyzed on an Accuri C6 flow cytometer (BD Biosciences). Binding of SIRPα-hIgG4 fusion proteins or anti-CD47 antibodies was detected with goat anti-human IgG antibody (Invitrogen) and was analyzed on an LSRFortessa with high-throughput sampler (BD Biosciences). Data represent the mean fluorescence intensity normalized to maximal binding for each class of reagents, and points were fit to sigmoidal dose-response curves using Prism 5 (Graphpad).

Cell-based CD47 blocking assays. Biotinylated WTa1d1 SIRPα was incubated with Alex Fluor 647-conjugated streptavidin to form WTa1d1 SIRPα tetramers. 100 nM WTa1d1 SIRPα tetramers were combined with titrating concentrations of CD47 antagonists and simultaneously added to 50,000 GFP-luciferase+ Raji cells. Cells were incubated for 30 min at 4° C. then washed to remove unbound tetramer. Samples were stained with DAPI (Sigma) to exclude dead cells, and fluorescence was assayed using an LSRFortessa with a high throughput sampler (BD Biosciences). Data represent the geometric mean fluorescence intensity analyzed using FlowJo v9.4.10 (Tree Star) normalized to maximal tetramer binding, and were fit to sigmoidal dose response curves using Prism 5 (Graphpad).

Macrophage derivation and phagocytosis assays. Leukocyte reduction system (LRS) chambers were obtained from the Stanford Blood Center from anonymous donors, and peripheral blood mononuclear cells were enriched by density gradient centrifugation over Ficoll-Paque Premium (GE Healthcare). Monocytes were purified on an AutoMACS (Miltenyi) using anti-CD14 microbeads (Miltenyi) and differentiated to macrophages by culture for 7-10 days in IMDM+GlutaMax (Invitrogen) supplemented with 10% AB-Human Serum (Invitrogen) and 100 U/mL penicillin and 100 µg/mL streptomycin (Invitrogen). Phagocytosis assays were performed by co-culture of 50,000 macrophages with 100,000 GFP+tumor cells for 2 hours, then analyzed using an LSRFortessa cell analyzer with high throughput sampler (BD Biosciences). Antibodies used for treatment included: mouse IgG1 isotype control (eBioscience), anti-CD47 clone 2D3 (eBioscience), anti-EpCam (BioLegend), cetuximab (Bristol-Myers Squibb), and rituximab (Genentech). Macrophages were identified by flow cytometry using anti-CD14, anti-CD45, or anti-CD206 antibodies (BioLegend). Dead cells were excluded from the analysis by staining with DAPI (Sigma). Phagocytosis was evaluated as the percentage of $GFP^+$ macrophages using FlowJo v9.4.10 (Tree Star) and was normalized to the maximal response by each independent donor against each cell line. Statistical significance was determined by 2-way ANOVA with Bonferroni post-tests, and, when indicated, data were fit to sigmoidal dose-response curves using Prism 5 (Graphpad).

Live-cell imaging of phagocytosis. $RFP^+$ mouse macrophages were generated and evaluated in live-cell imaging assays as previously described. Briefly, bone marrow cells were isolated from C57BL/$K_a$ Rosa26 mRFP1 transgenic mice and differentiated in 10 ng/ml murine M-CSF (Peprotech). 500,000 Raji cells were labeled with 0.5 µM CFSE (Invitrogen) and co-cultured with 50,000 RFP+ macrophages and imaged using a BioStation IMQ (Nikon) equilibrated to 37° C. and 5% carbon dioxide.

Mice. Nod.Cg-Prkdc$^{scid}$ IL2rg$_{tm1Wjl}$/SzJ (NSG) mice were used for all in vivo experiments. Mice were engrafted with tumors at approximately 6-10 weeks of age, and experiments were performed with age and sex-matched cohorts of 8-15 mice. Mice were maintained in a barrier facility under the care of the Stanford Veterinary Services Center and handled according to protocols approved by the Stanford University Administrative Panel on Laboratory Animal Care.

Tumor models. To model human colon cancer, $1 \cdot 10^5$ GFP-luciferase+ DLD-1 cells were injected into the peritoneal cavities of NSG mice. Tumor nodules were visualized on an M205 FA fluorescent dissecting microscope (Leica) fitted with a DFC 500 camera (Leica). Bladder cancer was modeled by engraftment of $1.25 \cdot 10^5$ GFP-luciferase$^+$ 639-V cells into the dorsal subcutaneous tissue of NSG mice in 25% Matrigel (BD Biosciences). $1 \cdot 10^6$ GFP-luciferase$^+$ Raji cells were engrafted subcutaneously on the lower flank for a localized model of human lymphoma. In all models, treatment was initiated upon confirmation of engraftment and continued as indicated. For all treatments, 200 µg SIRPα variant or antibody was administered by intraperitoneal injection on a daily schedule. Tumor growth was monitored by bioluminescence imaging, and tumor dimensions were measured to calculate volumes according to the ellipsoid formula ($\pi/6 \cdot length \cdot width^2$). Statistical significance was determined by Mann-Whitney test or Kruskal-Wallis with Dunn's post-tests as appropriate. Survival was analyzed by Mantel-Cox test.

Hematologic analysis. Blood was drawn from the retro-orbital plexus and collected in dipotassium-EDTA Micro-tainer tubes (BD Biosciences). Hematologic parameters were evaluated using a HemaTrue analyzer (Heska). Statistical significance was determined by 2-way ANOVA with Bonferroni post-test. Binding of SIRPα-Fc variants to mouse whole blood was determined by flow cytometry using Alexa Fluor 647 goat anti-human IgG antibody (Invitrogen).

Bioluminescence imaging. Anesthetized mice were injected with 200 µL D-luciferin (firefly) potassium salt (Biosynth) reconstituted at 16.67 mg/mL in sterile PBS. Bioluminescence imaging was performed using an IVIS Spectrum (Caliper Life Sciences) over 20 minutes to record maximal radiance. Peak total flux values were assessed from the anatomical region of interest using Living Image 4.0 (Caliper Life Sciences) and used for analysis.

Protein sequences. Among the proteins used in the examples described herein, the following are included:

FD6-hIgG4 (FD6 underlined, which includes the CH2, CH3 and hinge regions of human IgG4, and the d1 domain of high affinity SIRPα FD6:

(SEQ ID NO: 40)
EEEVQIIQPDKSVSVAAGESAILHCTITSLFPVGPIQWFRGAGPARVLIY

NQRQGPFPRVTTISETTRRENMDFSISISNITPADAGTYYCIKFRKGSPD

TEFKSGAGTELSVRAKPSAAAPPCPPCPAPEFLGGPSVFLFPPKPKDTLM

ISRTPEVTCVVVDVSQEDPEVQFNWYVDGVEVHNAKTKPREEQFNSTYRV

VSVLTVLHQDWLNGKEYKCKVSNKGLPSSIEKTISKAKGQPREPQVYTLP

PSQEEMTKNQVSLTCLVKGFYPSDIAVEWESNGQPENNYKTTPPVLDSDG

SFFLYSRLTVDKSRWQEGNVFSCSVMHEALHNHYTQKSLSLSPGK

CV1-hIgG4 (CV-1 underlined, human IgG4 S228P in bold), which includes the CH2, CH3 and hinge regions of human IgG4, and the d1 domain of high affinity SIRPα CV1. Note that the CV1 amino acid substitutions are "built" on the human wild-type allele 2:

(SEQ ID NO: 41)
EEELQIIQPDKSVLVAAGETATLRCTITSLFPVGPIQWFRGAGPGRVLIY

NQRQGPFPRVTTVSDTTKRNNMDFSIRIGNITPADAGTYYCIKFRKGSPD

DVEFKSGAGTELSVRAKPSAAAPPCPPCPAPEFLGGPSVFLFPPKPKDTL

MISRTPEVTCVVVDVSQEDPEVQFNWYVDGVEVHNAKTKPREEQFNSTYR

VVSVLTVLHQDWLNGKEYKCKVSNKGLPSSIEKTISKAKGQPREPQVYTL

PPSQEEMTKNQVSLTCLVKGFYPSDIAVEWESNGQPENNYKTTPPVLDSD

GSFFLYSRLTVDKSRWQEGNVFSCSVMHEALHNHYTQKSLSLSPGK

FD6-hIgG2 (FD6 underlined, human IgG2 in bold), which includes the CH2, CH3 and hinge regions of human IgG2, and the d1 domain of high affinity SIRPα FD6:

(SEQ ID NO: 42)
EEEVQIIQPDKSVSVAAGESAILHCTITSLFPVGPIQWFRGAGPARVLIY

NQRQGPFPRVTTISETTRRENMDFSISISNITPADAGTYYCIKFRKGSPD

TEFKSGAGTELSVRAKPSAAAVECPPCPAPPVAGPSVFLFPPKPKDTLMI

SRTPEVTCVVVDVSHEDPEVQFNWYVDGMEVHNAKTKPREEQFNSTFRVV

SVLTVVHQDWLNGKEYKCKVSNKGLPAPIEKTISKTKGQPREPQVYTLPP

SREEMTKNQVSLTCLVKGFYPSDIAVEWESNGQPENNYKTTPPMLDSDGS

FFLYSKLTVDKSRWQQGNVFSCSVMHEALHNHYTQKSLSLSPGK

CV1-hIgG2 (CV-1 underlined, human IgG2 in bold), which includes the CH2, CH3 and hinge regions of human IgG2, and the d1 domain of high affinity SIRPα CV-1:

(SEQ ID NO: 43)
EEELQIIQPDKSVLVAAGETATLRCTITSLFPVGPIQWFRGAGPGRVLIY

NQRQGPFPRVTTVSDTTKRNNMDFSIRIGNITPADAGTYYCIKFRKGSPD

DVEFKSGAGTELSVRAKPSAAAVECPPCPAPPVAGPSVFLFPPKPKDTLM

ISRTPEVTCVVVDVSHEDPEVQFNWYVDGMEVHNAKTKPREEQFNSTFRV

VSVLTVVHQDWLNGKEYKCKVSNKGLPAPIEKTISKTKGQPREPQVYTLP

PSREEMTKNQVSLTCLVKGFYPSDIAVEWESNGQPENNYKTTPPMLDSDG

SFFLYSKLTVDKSRWQQGNVFSCSVMHEALHNHYTQKSLSLSPGK

GCN4 Leuzine Zipper Fusions:

FD6-zipper (FD6 underlined, GCN4 leucine-zipper in bold), which includes the d1 domain of FD6 fused to GCN4, and which utilizes the leucine zipper function to dimerize:

(SEQ ID NO: 44)
EEEVQIIQPDKSVSVAAGESAILHCTITSLFPVGPIQWFRGAGPARVLIY

NQRQGPFPRVTTISETTRRENMDFSISISNITPADAGTYYCIKFRKGSPD

TEFKSGAGTELSVRAKPSAAARMKQLEDKVEELLSKNYHLENEVARLKKL

VGAASGAD

Concatamer Constructs:

FD6 concatamer (FD6 underlined, GGGGSGGGGS linker_SEQ ID NO: 45, residues 119-128, FD6 underlined)

(SEQ ID NO: 45)
EEEVQIIQPDKSVSVAAGESAILHCTITSLFPVGPIQWFRGAGPARVLIY

NQRQGPFPRVTTISETTRRENMDFSISISNITPADAGTYYCIKFRKGSPD

TEFKSGAGTELSVRAKPSGGGGSGGGGSEEEVQIIQPDKSVSVAAGESAI

LHCTITSLFPVGPIQWFRGAGPARVLIYNQRQGPFPRVTTISETTRRENM

DFSISISNITPADAGTYYCIKFRKGSPDTEFKSGAGTELSVRAKPS

| Table of Selected Sequences | | |
|---|---|---|
| SEQ ID NO: 1 | Native sequence, d1 domain | 118 aa Protein |
| SEQ ID NO: 2 | Native sequence, full length protein | 504 aa Protein |

| Table of Selected Sequences | | |
|---|---|---|
| SEQ ID NO: 3 | 1D4 mutant d1 domain | 118 aa Protein |
| SEQ ID NO: 4 | 1A5 mutant d1 domain | 118 aa Protein |
| SEQ ID NO: 5 | 2D3 mutant d1 domain | 118 aa Protein |
| SEQ ID NO: 6 | 2A10 mutant d1 domain | 118 aa Protein |
| SEQ ID NO: 7 | 2B5 mutant d1 domain | 118 aa Protein |
| SEQ ID NO: 8 | 2A2 mutant d1 domain | 118 aa Protein |
| SEQ ID NO: 9 | 2F5 mutant d1 domain | 118 aa Protein |
| SEQ ID NO: 10 | CV1 mutant d1 domain | 119 aa Protein |
| SEQ ID NO: 37 | FB3 mutant d1 domain | 118 aa Protein |

| Table of Selected Sequences | | |
|---|---|---|
| SEQ ID NO: 38 | FD6 mutant d1 domain | 118 aa Protein |
| SEQ ID NO: 39 | FA4 mutant d1 domain | 118 aa Protein |
| SEQ ID NO: 40 | FD6-hIgG4 | 345 aa Protein |
| SEQ ID NO: 41 | CV1-hIgG4 | 346 aa Protein |
| SEQ ID NO: 42 | FD6-hIgG2 | 344 aa Protein |
| SEQ ID NO: 43 | CV1-hIgG2 | 345 aa Protein |
| SEQ ID NO: 44 | GCN4 leuzine zipper | 158 aa Protein |
| SEQ ID NO: 45 | FD6 concatamer | 246 aa Protein |
| SEQ ID NO: 47 | 2B5 mutant d1 domain | 118 aa Protein |

What is claimed is:

1. A soluble human SIRPα polypeptide comprising the amino acid sequence of SEQ ID NO. 41.

2. A homodimeric polypeptide comprising the polypeptide of claim 1.

3. A therapeutic formulation comprising the polypeptide of claim 1, and a pharmaceutically acceptable excipient.

4. The therapeutic formulation of claim 3 in a unit dosage form comprising the polypeptide in a dose of 0.0001 to 100 milligram per kilogram (mg/kg) of body weight of a subject.

5. The therapeutic formulation of claim 4, wherein the dose is 1 to 10 mg/kg of body weight of the subject.

6. The therapeutic formulation of claim 4, wherein the dose is 0.01 to 5 mg/kg of body weight of the subject.

7. A method of increasing phagocytosis of a human cell expressing CD47 in a human subject, comprising administering a soluble human SIRPα polypeptide comprising the amino acid sequence of SEQ ID NO. 10 fused to an IgG4 Fc amino acid sequence wherein said IgG4 sequence comprises the IgG4 CH2, CH3 and hinge regions to the human subject in an amount effective to block the interaction between endogenous SIRPα and CD47.

8. The method of claim 7, wherein the amount is 0.0001 to 100 mg/kg of body weight of the human subject.

9. The method of claim 7, wherein the amount is 1 to 10 mg/kg of body weight of the human subject.

10. The method of claim 7, wherein the amount is 0.01 to 5 mg/kg of body weight of the human subject.

* * * * *